(12) United States Patent
Morgan et al.

(10) Patent No.: US 6,803,429 B2
(45) Date of Patent: Oct. 12, 2004

(54) SELECTIVE RING-OPENING CROSS-METATHESIS OF CYCLOOLEFINS

(75) Inventors: John P. Morgan, South Pasadena, CA (US); Christie Morrill, Pasadena, CA (US); Robert H. Grubbs, South Pasadena, CA (US); Tae-Lim Choi, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/114,674

(22) Filed: Apr. 1, 2002

(65) Prior Publication Data

US 2002/0198426 A1 Dec. 26, 2002

Related U.S. Application Data

(60) Provisional application No. 60/280,601, filed on Mar. 30, 2001.

(51) Int. Cl.$^7$ .............................. C08F 4/44; B01J 31/28
(52) U.S. Cl. ....................... 526/135; 526/145; 526/170; 526/172; 526/190; 526/192; 526/193; 526/204; 526/308; 526/340.3; 526/348.2; 548/103; 502/155; 502/167
(58) Field of Search ................................. 526/135, 145, 526/170, 172, 190, 192, 193, 204, 308, 340.3, 348.2; 548/103; 502/155, 167

(56) References Cited

U.S. PATENT DOCUMENTS

| | | | |
|---|---|---|---|
| 4,567,244 A | 1/1986 | Grubbs et al. | |
| 4,645,814 A | 2/1987 | Grubbs et al. | |
| 4,883,851 A | 11/1989 | Grubbs et al. | |
| 4,945,135 A | 7/1990 | Grubbs et al. | |
| 4,945,141 A | 7/1990 | Grubbs et al. | |
| 4,945,144 A | 7/1990 | Grubbs et al. | |
| 5,026,783 A | 6/1991 | Grubbs et al. | |
| 5,849,851 A | 12/1998 | Grubbs et al. | |
| 6,624,265 B2 * | 9/2003 | Grubbs et al. | ............. 526/135 |
| 2001/0034341 A1 | 10/2001 | Cuny et al. | |

OTHER PUBLICATIONS

Choi et al. (2001), "Olefin Metathesis Involving Ruthenium Enoic Carbene Complexes," *J. Am. Chem. Soc.* 123(42):10417–10418.

La et al. (2001), "Catalytic Asymmetric Ring–Opening Metathesis/Cross Metathesis (AROM/CM) Reactions. Mechanism and Application to Enantioselective Synthesis of Functionalized Cyclopentanes," *J. Am. Chem. Soc.* 123(32):7767–7778.

Limanto et al. (2000), "Sequential Intramolecular Cyclobutadiene Cycloaddition, Ring–Opening Metathesis, and Cope Rearrangement: Total Syntheses of (+)–and (–)–Asteriscanolide," *J. Am. Chem. Soc.* 122(33):8071–8072.

Morgan et al. (2002), "Selective Ring Opening Cross Metathesis of Cyclooctadiene and Trisubstituted Cycloolefins," *Organic Letters* 4(1):67–70.

Randl et al. (2001), "Ring Opening–Cross Metathesis of Unstrained Cycloalkenes," *Chem. Commun.* pp. 1796–1797.

Scholl et al. (1999), "Synthesis and Activity of a New Generation of Ruthenium–Based Olefin Metathesis Catalysts Coordinated with 1,3–Dimesityl-4,5–Dihydroimidazol–2–Ylidene Ligands," *Organic Letters* 1(6):953–956.

Snapper et al. (1997), "Regio– and Stereoselective Ring–Opening Cross–Metathesis. Rapid Entry into Fuctionalized Bicyclo[6.3.0] Ring Systems," *J. Am. Chem. Soc.* 119(6):1478–1479.

Stüer et al. (1998), "Carbynehydridoruthenium Complexes as Catalysts for the Selective, Ring–Opening Metathesis of Cyclopentene with Methyl Acrylate," *Angew. Chem. Int. Ed.* 37(24):3421–3423.

Randall et al. (1995), "Selective Ring–Opening Cross–Metathesis. Short Syntheses of Multifidene and Viridiene," *J. Am. Chem. Soc.* 117(37):9610–9611.

* cited by examiner

*Primary Examiner*—Robert D. Harlan
(74) *Attorney, Agent, or Firm*—Dianne E. Reed; Reed & Eberle LLP

(57) ABSTRACT

A catalytic method is provided for a ring-opening cross-metathesis reaction between a cycloolefinic substrate and a second olefinic reactant, wherein the catalyst used is a transition metal alkylidene complex substituted with an N-heterocyclic carbene ligand. The substrates are selected so that the rate of the cross-metathesis reaction of the second olefinic reactant, $k_{CM}$, is greater than or equal to the rate of the ring-opening metathesis reaction, $k_{RO}$. In this way, the predominant ROCM product is a monomer, dimer, and/or oligomer, but not a polymer. The invention additionally provides for selective production of an end-differentiated olefinic product, using trisubstituted cycloolefins as substrates and/or a subsequent cross-metathesis reaction following an initial ROCM step. The cycloolefinic substrates include low-strain olefins such as cyclohexene as well as higher strain olefins such as cyclooctene.

26 Claims, 2 Drawing Sheets

SELECTIVE RING-OPENING CROSS-METATHESIS OF CYCLOOLEFINS

CROSS-REFERENCE TO RELATED APPLICATIONS

This application claims priority of Provisional Application Ser. No. 60/280,601, filed Mar. 30, 2001.

This application claims priority under 35 U.S.C. §119(e)(1) to U.S. Provisional Patent Application Serial No. 60/280,601, filed Mar. 30, 2001. The disclosure of the aforementioned application is incorporated by reference in its entirety.

ACKNOWLEDGEMENT OF GOVERNMENT SUPPORT

This invention was developed with U.S. Government support under grant number 5 R01 GM31332 awarded by the National Institutes of Health. The Government has certain rights in the invention.

TECHNICAL FIELD

This invention relates generally to a method for carrying out an olefin metathesis reaction using a Group 8 transition metal complex as a catalyst. More particularly, the invention relates to a method for carrying out a ring-opening cross-metathesis ("ROCM") reaction using the aforementioned catalyst, in which a cycloolefin and a second olefinic reactant are selected with respect to their relative reactivity in the ROCM reaction. Methods are also provided for the catalysis of regioselective ROCM reactions and ROCM reactions involving at least one functionalized olefinic reactant.

BACKGROUND OF THE INVENTION

The flexibility of the olefin metathesis reaction allows the efficient production of highly functionalized, unsaturated polymers and small molecules. Grubbs et al. (1998) *Tetrahedron* 54, 4413–4450; Randall et al. (1998) *J. Mol. Cat. A-Chem.* 133, 29–40; Trnka and Grubbs (2001) *Acc. Chem. Res.* 34, 18–29. Many synthetically relevant applications that involve more than one type of metathetical transformation utilize ruthenium catalysts such as (I) and molybdenum catalysts such as (II)

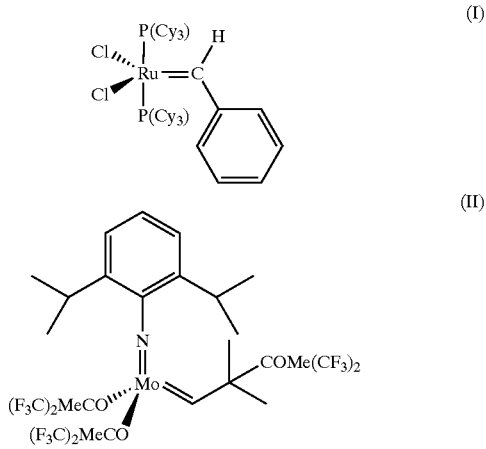

wherein "Cy" is a cycloalkyl group such as cyclohexyl or cyclopentyl. See Schwab et al. (1995) *Angew. Chem., Int. Ed. Engl.* 34, 2039–2041; Schwab et al. (1996) *J. Am. Chem. Soc.* 118, 100–110. Notably, the combination of ring-opening metathesis polymerization (ROMP) and cross-metathesis (CM) produces unique telechelic and multiple-block copolymers with novel properties. Chung et al. (1992) *Macromolecules* 25, 5137–5144; Hillmyer et al. (1997) *Macromolecules* 30, 718–721; Maughon et al. (2000) *Macromolecules* 33, 1929–1935; Morita et al. (2000) *Macromolecules* 33, 6621–6623; Bielawski et al. (2000) *Angew. Chem. Int. Ed. Engl.* 39:2903–2906. For a review on telechelic polymers, see E. J. Goethals, Telechelic Polymers: Synthesis and Applications, CRC, Boca Raton, Fla., 1989. The synthesis of substituted polyethers has also been achieved by the ring closing metathesis (RCM) of a short linear molecule followed by ROMP of this new monomer. Marsella et al. (1997) *Angew. Chem. Int. Ed. Engl.* 36, 1101–1103; Maynard et al. (1999) *Macromolecules* 32, 6917–6924. With regard to small molecules, ring opening-ring closing "tandem" sequences allow the rapid construction of mutiply fused ring systems, which include those in complex natural products. In each of these cases the product of one metathesis event is directly available for the next, which allows multiple metathesis routes to be synthetically exploite d.

A variation on this theme that remains largely unexplored is ring-opening cross-metathesis ("ROCM"), illustrated in the following scheme:

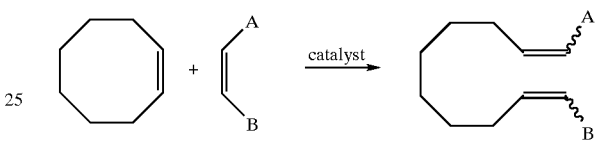

ROCM actually involves a tandem sequence in which a cycloolefin is opened and a second, acyclic olefin is then crossed onto the newly formed termini. The wide synthetic availability of cycloolefins makes this route attractive, and cyclic compounds are particularly important in synthesis. Most significantly, ring systems are key to stereochemical control; the understanding of ring conformation often presents the most expeditious route for stereocenter installation. The ability to take these general carbocycles to highly functionalized linear molecules (which, ideally, would have differentially protected termini) would therefore be extremely valuable to the synthetic chemist.

Previous work in this area has focused on highly strained cyclobutene and norbornene derivatives, as illustrated in the following schemes:

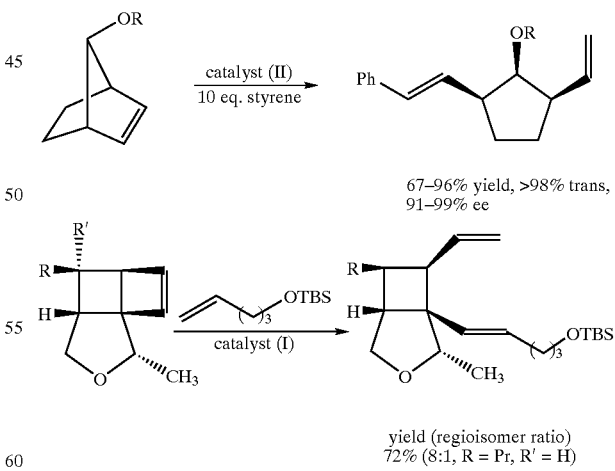

Randall et al. (1995) *J. Am. Chem. Soc.* 117:9610–9611; Snapper et al. (1997) *J. Am. Chem. Soc.* 119:1478–1479; Limanto et al. (2000) *J. Am. Chem. Soc.* 122:8071–8072; Schrader et al. (2000) *Tetrahedron Lett.* 41:9685–9689.

Both systems typically utilize steric congestion to disfavor ROMP relative to ROCM, which imposes stringent restrictions on the scaffolds open to this synthetic method. A more practical route would involve systems in which cross-metathesis can compete with polymerization, thereby directly limiting the size of the molecules produced. The invention is addressed, in part, to such a catalytic reaction, wherein the reactants as well as the catalyst are selected to maximize production of a monomeric or oligomeric product relative to the production of a telechelic polymer, via an ROCM route. The invention is also addressed to a method for producing monomers and oligomers that are "end differentiated" rather than symmetrical, enhancing the selectivity and versatility of the ROCM reaction products in further synthetic processes.

Recently, significant interest has focused on the use of N-heterocyclic carbene ligands as superior alternatives to phosphines. See, e.g., Trnka and Grubbs, supra; Bourissou et al. (2000) *Chem. Rev.* 100:39–91; Scholl et al. (1999) *Tet. Lett.* 40:2247–2250; Scholl et al. (1999) *Organic Lett.* 1(6):953–956; and Huang et al. (1999) *J. Am. Chem. Soc.* 121:2674–2678. N-heterocyclic carbene ligands offer many advantages, including readily tunable steric bulk, vastly increased electron donor character, and compatibility with a variety of metal species. In addition, replacement of one of the phosphine ligands in these complexes significantly improves thermal stability. The vast majority of research on these carbene ligands has focused on their generation and isolation, a feat finally accomplished by Arduengo and coworkers within the last ten years (see, e.g., Arduengo et al. (1999) *Acc. Chem. Res.* 32:913–921). Representative of these second generation catalysts are the four ruthenium complexes (IVA), (IVB), (VA) and (VB):

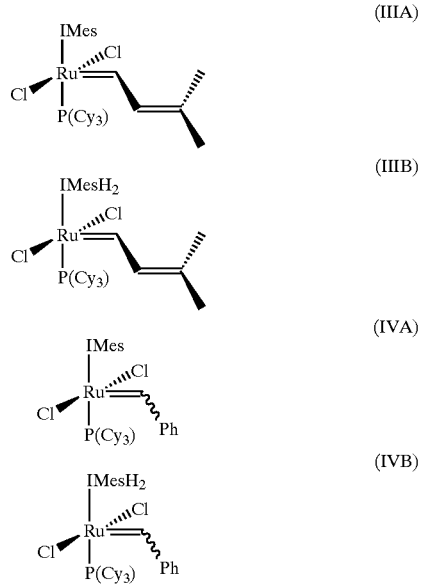

In the above structures, Cy is as defined previously, "IMes" represents 1,3-dimesityl-imidazol-2-ylidene IMes:

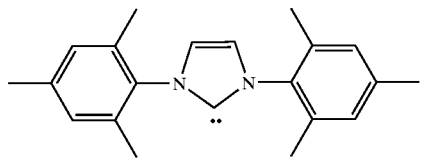

and "IMesH$_2$" represents 1,3-dimesityl-4,5-dihydroimidazol-2-ylidene

IMesH$_2$:

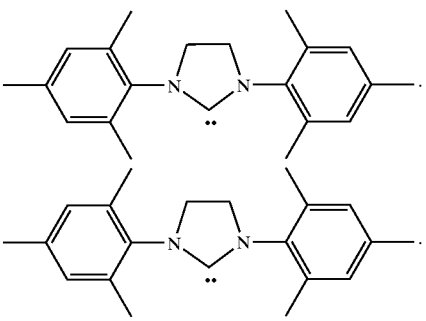

These transition metal carbene complexes, particularly those containing a ligand having the 4,5-dihydroimidazol-2-ylidene structure such as in IMesH$_2$, have been found to address a number of previously unsolved problems in olefin metathesis reactions, and are the preferred catalysts for use in conjunction with the novel ROCM methodology.

SUMMARY OF THE INVENTION

The present invention is addressed to the aforementioned need in the art, and provides a novel process for carrying out selective ring opening cross metathesis of a cycloolefin, which may or may not be a strained cyclic structure. More specifically, the method involves a catalyzed ring-opening cross-metathesis (ROCM) reaction between a cyclic olefin and a second olefinic reactant, wherein the cyclic olefin is contacted with the second olefinic reactant in the presence of a Group 8 transition metal alkylidene catalyst under conditions and for a time period effective to allow the ROCM reaction to occur. The catalyst has the structure of formula (V)

in which:

M is a Group 8 transition metal, particularly Ru or Os;

X$^1$ and X$^2$ may be the same or different, and are anionic ligands or polymers;

R$^1$ is selected from the group consisting of hydrogen, hydrocarbyl, substituted hydrocarbyl, heteroatom-containing hydrocarbyl, substituted heteroatom-containing hydrocarbyl, and carboxyl;

R$^2$ is selected from the group consisting of hydrogen, hydrocarbyl, substituted hydrocarbyl, heteroatom-containing hydrocarbyl, and substituted heteroatom-containing hydrocarbyl;

L is a neutral electron donor ligand; and $L^1$ is a neutral electron donor ligand having the structure of formula (VI)

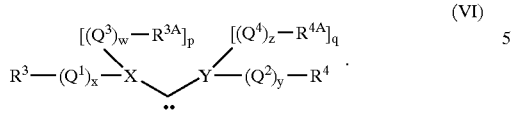

(VI)

In structure (VI):

X and Y are heteroatoms selected from N, O, S, and P;

p is zero when X is O or S, and is 1 when X is N or P;

q is zero when Y is O or S, and is 1 when Y is N or P;

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—;

w, x, y and z are independently zero or 1; and $R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein any two or more of $X^1$, $X^2$, L, $R^1$, $R^2$, $R^3$, $R^{3A}$, $R^4$, and $R^{4A}$ can be taken together to form a chelating multidentate ligand.

Accordingly, the complex of formula (V) may also be represented as (VII)

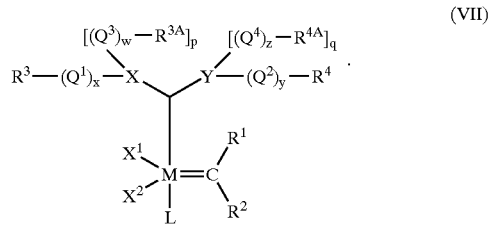

(VII)

In a preferred embodiment, L is an N-heterocyclic carbene having the structure of formula (VIII)

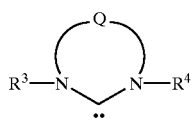

(VIII)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage. Accordingly, the metal carbene complex of formula (VII) may also be represented as follows:

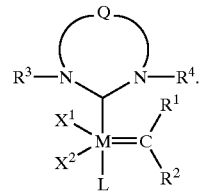

(IX)

It will be appreciated that a metathesis reaction between a cyclic olefin and a second olefinic reactant can result in several different types of reaction products, depending, in large part, on the relative rates of the ring-opening metathesis reaction and the cross-metathesis reaction between the second olefinic reactant and the cyclic olefin.

Accordingly, given that a cyclic olefin will undergo a ring opening reaction in the presence of the catalyst at a rate $k_{RO}$, and that the second olefinic reactant will undergo a cross-metathesis reaction with the cycloolefin at a rate $k_{CM}$, the invention in another embodiment involves selection of the two reactants such that the approximate relationship of $k_{RO}$ to $k_{CM}$ is already known, i.e., predetermined. See Morgan et al. (2002) *Organic Letters* 4(1):67–70, the disclosure of which is incorporated by reference. As will be explained in further detail infra, when $k_{CM}$ is greater than or equal to $k_{RO}$, the ROCM product is predominantly a monomer, dimer, and/or oligomer, but not a polymer. More specifically, when $k_{CM}$ is approximately equal to $k_{RO}$, the ROCM product is predominantly a dimer or oligomer, while when $k_{CM}$ is greater than $k_{RO}$, the ROCM product is predominantly a monomer. Dimers and oligomers are of particular interest because their internal olefin moieties may be further functionalized by metathesis or other transformations.

Monomers are of interest as well, however, particularly when they can be prepared so as to be end differentiated, i.e., asymmetric with regard to the two terminal olefinic groups resulting from the ROCM reaction. It will be appreciated that $k_{RO}$ will be higher for moderately and highly strained cycloolefins such as cyclooctadiene, but lower for low-strain olefins such as cyclopentene and cyclohexene. Accordingly, in another embodiment, the invention pertains to an ROCM reaction in which $k_{CM}$ is sufficiently greater than $k_{RO}$, so as to result in a predominantly monomeric product.

The invention additionally pertains to methods for selectively synthesizing an end-differentiated olefinic product, as alluded to above. In this case, the choice of cyclic olefin is relevant, insofar as a 1,1,2-trisubstituted olefin will preferentially result in an asymmetrically terminated olefinic product. Alternatively, or in addition, end differentiation can be achieved in a two-step process wherein, initially, a first ROCM step is carried out as above, and a second step involves a simple cross metathesis reaction of an additional olefin with the ROCM product. In the latter step, the catalyst may or may not have the structure of formula (VII). Alternative catalysts for the second, cross-metathesis reaction include, for example, bisphosphine complexes, e.g., complexes having the structure of formula (V) wherein L and $L^1$ are phosphines of the formula $PR^5R^6R^7$, where $R^5$, $R^6$, and $R^7$ are each independently aryl or $C_1$–$C_{10}$ alkyl, particularly primary alkyl, secondary alkyl or cycloalkyl (such as —P(cyclohexyl)$_3$, —P(cyclopentyl)$_3$, —P(isopropyl)$_3$, —P(phenyl)$_3$, —P(phenyl)$_2$(alkyl) and —P(phenyl)(alkyl)$_2$). Such end differentiated olefinic products, by virtue of their asymmetry, have enhanced utility with regard to subsequent synthetic processes.

DETAILED DESCRIPTION OF THE INVENTION

Figure 1:
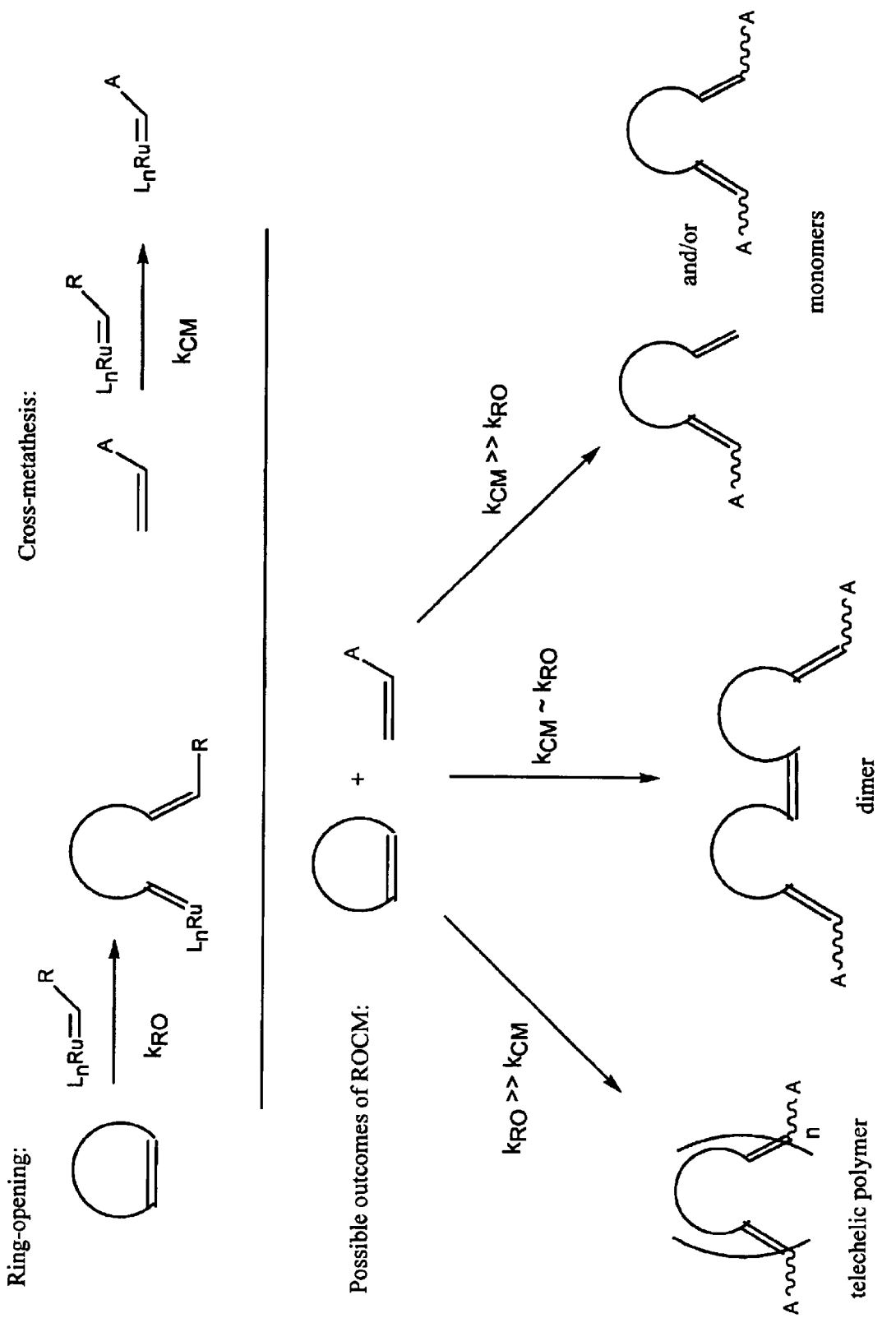
FIG. 1 schematically illustrates the possible outcomes of an ROCM reaction involving a cyclic olefin and a second olefinic reactant.

I. Definitions and Nomenclature:

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a solvent" includes a single solvent as well as solvent mixture, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched or cyclic saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched or cyclic alkyl group, where "alkyl" is as defined above.

The term "alkenyl" as used herein refers to a linear, branched or cyclic hydrocarbon group of 2 to 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched or cyclic alkenyl group, where "alkenyl" is as defined above.

The term "alkynyl" as used herein refers to a linear or branched hydrocarbon group of 2 to 20 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkenyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety), generally containing in the range of 5 to 24 carbon atoms. Preferred aryl groups contain one aromatic ring or 2 to 4 fused or linked aromatic rings, e.g., phenyl, naphthyl, biphenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage. An "aryloxy" group may be represented as —O-aryl where aryl is as defined above.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The term "alicyclic" refers to an aliphatic cyclic moiety, which may or may not be bicyclic or polycyclic.

The term "amino" is used herein to refer to the group —NZ$^1$Z$^2$, where each of Z$^1$ and Z$^2$ is independently selected from the group consisting of hydrogen and optionally substituted alkyl, alkenyl, alkynyl, aryl, aralkyl, alkaryl and heterocyclic.

The term "acroyl" refers to any a,β-unsaturated carbonyl system. An acroyl group may be substituted (e.g., alkyl- and/or aryl-substituted) and/or heteroatom-containing.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety at least one hydrogen atom bound to a carbon (or other) atom is replaced with one or more non-hydrogen substituents. Examples of such substituents include, without limitation: functional groups such as halogen, phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_1$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, or boryl, or a metal-containing or metalloid-containing group (wherein the metal may be, for example, Sn or Ge); and the hydrocarbyl moieties $C_1$–$C_{20}$ alkyl, $C_2$–$C_{20}$ alkenyl, $C_2$–$C_{20}$ alkynyl, $C_5$–$C_{20}$ aryl, $C_5$–$C_{30}$ aralkyl, and $C_5$–$C_{30}$ alkaryl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "polymer" refers to a chemical compound comprised of at least 20 monomer units, and the term "oligomer" refers to a chemical compound comprised of fewer than 20 monomer units.

The term "stereoselective" refers to a chemical reaction that preferentially results in one stereoisomer relative to a second stereoisomer, i.e., gives rise to a product in which the ratio of a desired stereoisomer to a less desired stereoisomer is greater than 1:1.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. The Catalyst:

The ring-opening cross-metathesis reactions of the invention are carried out catalytically, using a Group 8 transition metal complex that preferably contains two different ligands. These transition metal carbene complexes include a metal center in a +2 oxidation state, have an electron count of 16, and are penta-coordinated. More specifically, the preferred catalysts herein have the structure of formula (VII)

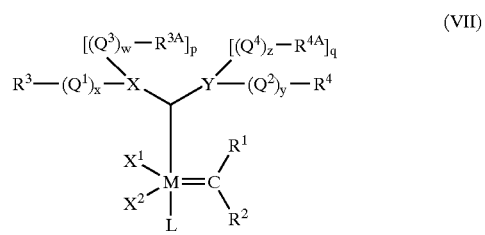

(VII)

wherein the various substituents are as follows:

M, which serves as the transition metal center in the +2 oxidation state, is a Group 8 transition metal, particularly ruthenium or osmium. In a preferred embodiment, M is ruthenium.

$X^1$ and $X^2$ are anionic ligands or polymers, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$–$C_{20}$ alkyl, $C_5$–$C_{20}$ aryl, $C_1$–$C_{20}$ alkoxy, $C_5$–$C_{20}$ aryloxy, $C_3$–$C_{20}$ alkyldiketonate, $C_5$–$C_{20}$ aryldiketonate, $C_2$–$C_{20}$ alkoxycarbonyl, $C_5$–$C_{20}$ aryloxycarbonyl, $C_2$–$C_{20}$ acyl, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl. Optionally, $X^1$ and $X^2$ may be substituted with one or more moieties selected from the group consisting of $C_1$–$C_{10}$ alkyl, $C_1$–$C_{10}$ alkoxy, aryl, and halide, which may, in turn, with the exception of halide, be further substituted with one or more groups selected from halide, $C_1$–$C_6$ alkyl, $C_1$–$C_6$ alkoxy, and phenyl. In more preferred embodiments, $X^1$ and $X^2$ are halide, benzoate, $C_2$–$C_6$ acyl, $C_2$–$C_6$ alkoxycarbonyl, $C_1$–$C_6$ alkyl, phenoxy, $C_1$–$C_6$ alkoxy, $C_1$–$C_6$ alkylsulfanyl, aryl, or $C_1$–$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride. The complex may also be attached to a solid support, such as to a polymeric substrate, and this attachment may be effected by means of $X^1$ and/or $X^2$, in which case $X^1$ and/or $X^2$ is a polymer.

$R^1$ is selected from the group consisting of hydrogen, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl, alkenyl, alkynyl, aryl, aralkyl, alkaryl, etc.), and carboxyl, and $R^2$ is selected from the group consisting of hydrogen, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl, alkenyl, alkynyl, aryl, aralkyl, alkaryl, etc.). $R^1$ and $R^2$ may also be linked to form a cyclic group, which may be aliphatic or aromatic, and may contain substituents and/or heteroatoms. Generally, such a cyclic group will contain 4 to 12, preferably 5 to 8, ring atoms.

In preferred catalysts, the $R^1$ substituent is hydrogen and the $R^2$ substituent is selected from the group consisting of $C_1$–$C_{20}$ alkyl, $C_2$–$C_{20}$ alkenyl, and aryl. More preferably, $R^2$ is phenyl, vinyl, methyl, isopropyl, or t-butyl, optionally substituted with one or more moieties selected from the group consisting of $C_1$–$C_6$ alkyl, $C_1$–$C_6$ alkoxy, phenyl, and a functional group Fn. Still more preferably, $R^2$ is phenyl or vinyl substituted with one or more moieties selected from the group consisting of methyl, ethyl, chloro, bromo, iodo fluoro, nitro, dimethylamino, methyl, methoxy, and phenyl. In the most preferred embodiments, the $R^2$ substituent is phenyl or —C=C(CH$_3$)$_2$.

L is a neutral electron donor ligand, and may or may not be linked to $R^2$. Examples of suitable L moieties include, without limitation, phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. In more preferred embodiments, L is a phosphine of the formula $PR^5R^6R^7$, where $R^5$, $R^6$, and $R^7$ are each independently aryl or $C_1$–$C_{10}$ alkyl, particularly primary alkyl, secondary alkyl or cycloalkyl. In the most preferred embodiments, L is selected from the group consisting of —P(cyclohexyl)$_3$, —P(cyclopentyl)$_3$, —P(isopropyl)$_3$, —P(phenyl)$_3$, —P(phenyl)$_2$(R$^7$) and —P(phenyl)(R$^7$)$_2$, in which R$^7$ is alkyl, typically lower alkyl. Also preferred are weaker ligands such as the nitrogen-containing heterocycles, which enhance catalytic activity presumably because of the requirement that the L ligand dissociate for initiation to occur. Examples of complexes wherein L and $R^2$ are linked include the following:

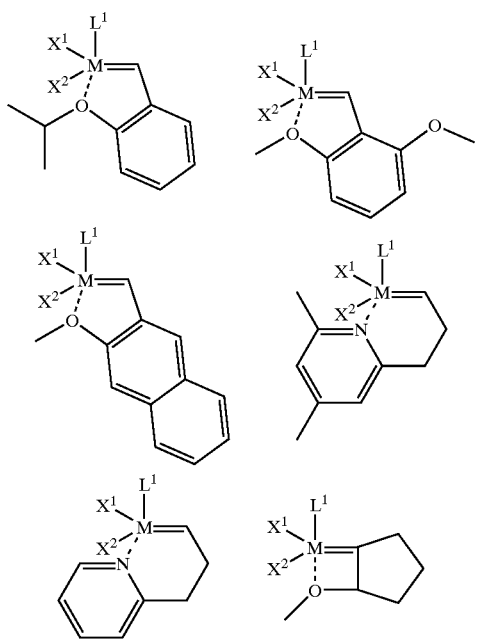

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y and z are independently zero or 1, meaning that each linker is optional. Preferably, w, x, y and z are all zero.

$R^3$, $R^{3A}$, $R^4$ and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein $R^{3A}$ and $R^{4A}$ may be linked to form a cyclic group.

It should be emphasized that any two or more (typically two, three or four) of $X^1$, $X^2$, L, $R^1$, $R^2$, $R^3$, $R^{3A}$, $R^4$, and $R^{4A}$ can be taken together to form a chelating multidentate ligand, as disclosed, for example, in U.S. Pat. No. 5,312,940 to Grubbs et al. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$— and —OC(CH$_3$)$_2$(CH$_3$)$_2$CO—. Preferred bidentate ligands are —P(Ph)$_2$ CH$_2$CH$_2$P(Ph)$_2$— and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, L, $R^1$, $R^2$, $R^3$, $R^{3A}$, $R^4$, and $R^{4A}$ (e.g., X, L, and any one of $R^3$, $R^{3A}$, $R^4$, and $R^{4A}$) are taken together to be cyclopentadienyl, indenyl or fluorenyl, each optionally substituted with $C_2$–$C_{20}$ alkenyl, $C_2$–$C_{20}$ alkynyl, $C_1$–$C_{20}$ alkyl, $C_5$–$C_{20}$ aryl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl, each of which may be further substituted with $C_1$–$C_6$ alkyl, halogen, $C_1$–$C_6$ alkoxy or with a phenyl group optionally substituted with halogen, $C_1$–$C_6$ alkyl or $C_1$–$C_6$ alkoxy. More preferably, in compounds of this type, X, L, and any one of $R^3$, $R^{3A}$, $R^4$, and $R^{4A}$ are taken together to be cyclopentadienyl or indenyl, each optionally substituted with vinyl, $C_1$–$C_{10}$ alkyl, $C_5$–$C_{20}$ aryl, $C_1$–$C_{10}$ carboxylate, $C_2$–$C_{10}$ alkoxycarbonyl, $C_1$–$C_{10}$ alkoxy, $C_5$–$C_{20}$ aryloxy, each optionally substituted with $C_1$–$C_6$ alkyl, halogen, $C_1$–$C_6$ alkoxy or with a phenyl group optionally substituted with halogen, $C_1$–$C_6$ alkyl or $C_1$–$C_6$ alkoxy. Most preferably, X, L, and any one of $R^3$, $R^{3A}$, $R^4$, and $R^{4A}$ may be taken together to be cyclopentadienyl, optionally substituted with vinyl, hydrogen, Me or Ph. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

In a preferred embodiment, the catalyst has the structure of formula (IX)

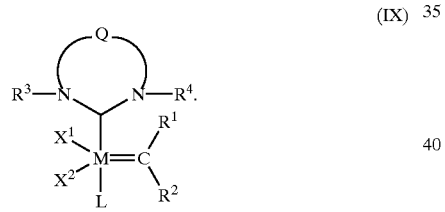

(IX)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to five cyclic groups. Q is often, although again not necessarily, a two-atom linkage or a three-atom linkage, e.g., —CH$_2$—CH$_2$—, —CH(Ph)—CH(Ph)— where Ph is phenyl; =CR—N=, giving rise to an unsubstituted (when R=H) or substituted (R=other than H) triazolyl group; and —CH$_2$—SiR$_2$—CH$_2$— (where R is H, alkyl, alkoxy, etc.).

In a more preferred embodiment, Q is a two-atom linkage having the structure —CR$^8$R$^{8A}$—CR$^9$R$^{9A}$— or —CR$^8$=CR$^9$—, more preferably —CR$^8$R$^{8A}$—CR$^9$R$^{9A}$—, in which case the complex has the structure of formula (X)

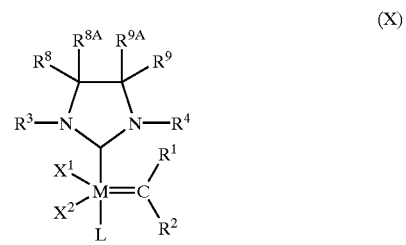

(X)

wherein $R^8$, $R^{8A}$, $R^9$, and $R^{9A}$ are independently selected from the group consisting of hydrogen, hydrocarbyl, substituted hydrocarbyl, heteroatom-containing hydrocarbyl, substituted heteroatom-containing hydrocarbyl, and may comprise a functional group. Examples of functional groups here include $C_1$–$C_{20}$ alkyl, $C_2$–$C_{20}$ alkenyl, $C_2$–$C_{20}$ alkynyl, $C_5$–$C_{20}$ aryl, carboxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkoxycarbonyl, $C_2$–$C_{20}$ alkoxycarbonyl, $C_1$–$C_{20}$ alkylthio, $C_5$–$C_{20}$ arylthio, $C_1$–$C_{20}$ alkylsulfonyl, and $C_1$–$C_{20}$ alkylsulfinyl, optionally substituted with one or more moieties selected from the group consisting of $C_1$–$C_{10}$ alkyl, $C_1$–$C_{10}$ alkoxy, $C_5$–$C_{20}$ aryl, hydroxyl, sulfhydryl, —(CO)—H, and halide.

Additionally, any two of $R^8$, $R^{8A}$, $R^9$, and $R^{9A}$ may be linked together to form a substituted or unsubstituted, saturated or unsaturated ring structure, e.g., a $C_4$–$C_{12}$ alicyclic group or a $C_5$ or $C_6$ aryl group, which may itself be substituted, e.g., with linked or fused alicyclic or aromatic groups, or with other substituents.

Examples of N-heterocyclic carbene ligands incorporated into complex (X) thus include, but are not limited to, the following:

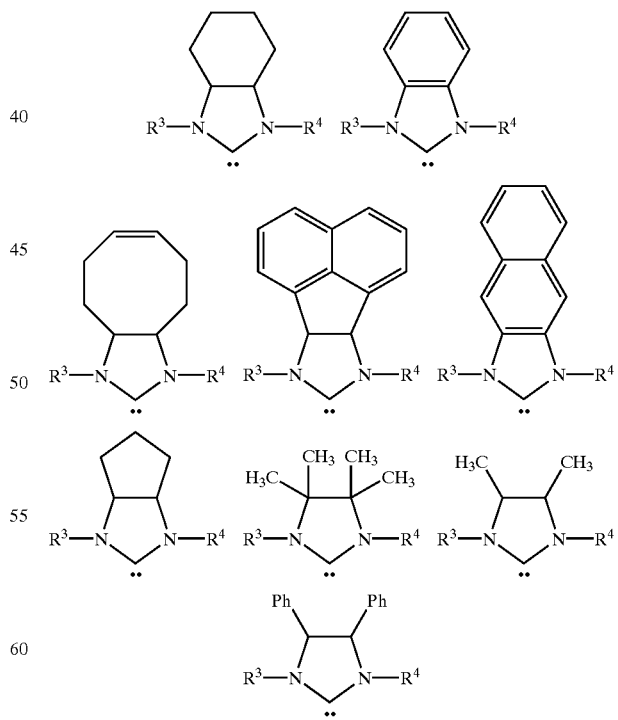

$R^3$ and $R^4$ are preferably aromatic, substituted aromatic, heteroaromatic, substituted heteroaromatic, alicyclic, or substituted alicyclic, composed of from one to about five cyclic groups. When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and have the structure (XI)

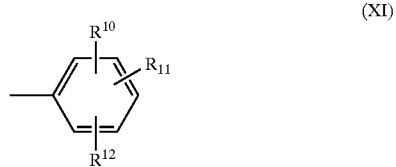

(XI)

in which $R^{10}$, $R^{11}$, and $R^{12}$ are each independently hydrogen, $C_1$–$C_{20}$ alkyl, substituted $C_1$–$C_{20}$ alkyl, $C_1$–$C_{20}$ heteroalkyl, substituted $C_1$–$C_{20}$ heteroalkyl, $C_5$–$C_{20}$ aryl, substituted $C_5$–$C_{20}$ aryl, $C_5$–$C_{20}$ heteroaryl, $C_5$–$C_{30}$ aralkyl, $C_5$–$C_{30}$ alkaryl, or halogen.

In especially preferred embodiments, $R^{10}$, $R^{11}$, and $R^{12}$ are each independently selected from the group consisting of hydrogen, methyl, ethyl, propyl, isopropyl, hydroxyl, halogen, phenyl, and lower alkyl-substituted phenyl (e.g., dimethylphenyl; see structure (XIII), infra). In the most preferred embodiments, $R^{10}$, $R^{11}$, and $R^{12}$ are the same and are each methyl.

When $R^3$ and $R^4$ are alicyclic, they are generally composed of a $C_7$–$C_{20}$, preferably a $C_7$–$C_{12}$, alicyclic structure, e.g., diisopinocamphenyl. Complexes formed with such ligands are exemplified by the complex containing the diisopinocamphenyl-substituted ligand shown in structural formula (XII), preparation of which is described in Example 4.

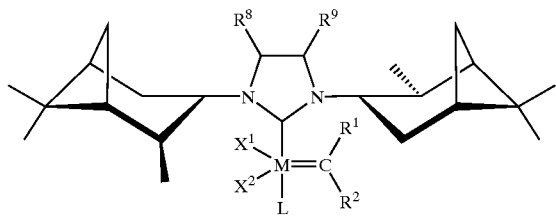

(XII)

In another preferred embodiment, $R^3$ and $R^4$ are each biphenylyl or substituted biphenylyl. Catalysts formed with such ligands are exemplified by the complex containing the 2,4,2',6'-tetramethylbiphenylyl-(i.e., 2,6-dimethyl-3-(2',6'-dimethylphenyl)phenyl-) substituted ligand shown below as structural formula (XIII), preparation of which is described in Example 5.

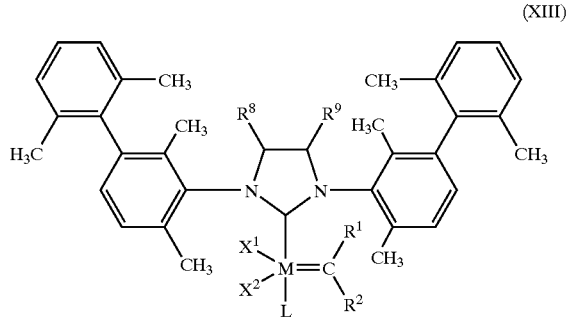

(XIII)

Ligands containing bulky, electron-donating groups such as those illustrated in the complexes of formulae (XII) and (XIII) provide for very highly active olefin metathesis catalysts. Such catalysts are thus suitable to catalyze reactions for which other, less active catalysts are ineffective, and are also useful in enhancing the stereoselectivity of a catalyzed cross-metathesis reaction.

Examples of more preferred catalysts useful in conjunction with the present methods, then, include, but are not limited to, the following:

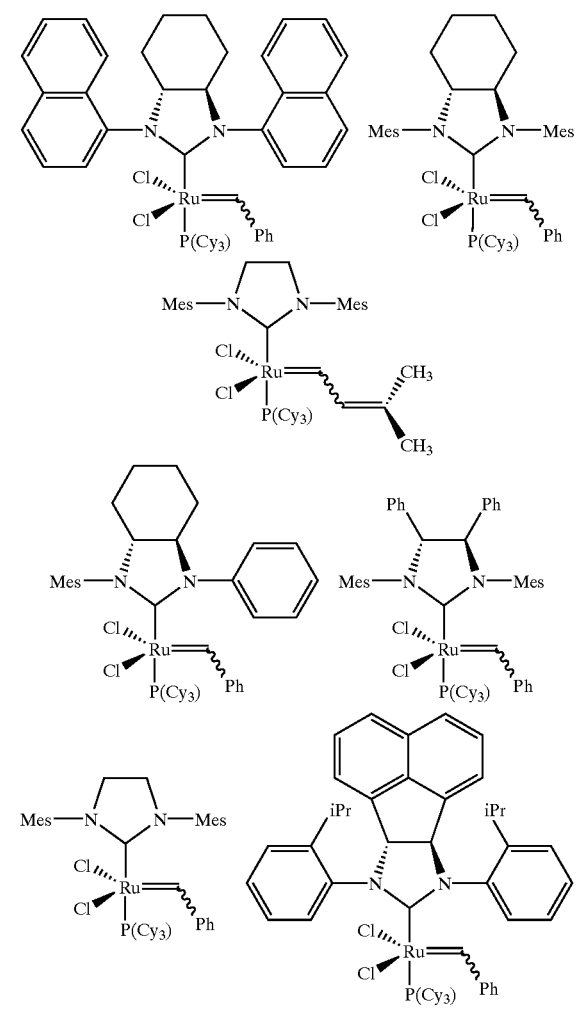

In the above molecular structures, "Mes" represents mesityl (2,4,6-trimethylphenyl), "iPr" is isopropyl, "Ph" is phenyl, and "Cy" is cyclohexyl.

III. Ring-opening Cross-metathesis Reactions:

The ROCM reaction catalyzed by the complexes described above involve a cyclic olefin and a second olefinic reactant, wherein the two reactants are brought into contact in the presence of a catalytically effective amount of the complex, under conditions and for a time period effective to allow the ROCM reaction to occur. In general, the cyclic olefin may be represented by the structure of formula (XIV)

(XIV)

wherein J and $R^{13}$ are as follows:

$R^{13}$ is selected from the group consisting of hydrogen, hydrocarbyl (e.g., $C_1-C_{20}$ alkyl, $C_5-C_{20}$ aryl, $C_5-C_{30}$ aralkyl, or $C_5-C_{30}$ alkaryl), substituted hydrocarbyl (e.g., substituted $C_1-C_{20}$ alkyl, $C_5-C_{20}$ aryl, $C_5-C_{30}$ aralkyl, or $C_5-C_{30}$ alkaryl), heteroatom-containing hydrocarbyl (e.g., $C_1-C_{20}$ heteroalkyl, $C_5-C_{20}$heteroaryl, heteroatom-containing $C_5-C_{30}$ aralkyl, or heteroatom-containing $C_5-C_{30}$ alkaryl), and substituted heteroatom-containing hydrocarbyl (e.g., substituted $C_1-C_{20}$ heteroalkyl, $C_5-C_{20}$heteroaryl, heteroatom-containing $C_5-C_{30}$ aralkyl, or heteroatom-containing $C_5-C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1-C_{20}$ alkylsulfanyl, $C_5-C_{20}$ arylsulfanyl, $C_1-C_{20}$ alkylsulfonyl, $C_5-C_{20}$ arylsulfonyl, $C_1-C_{20}$ alkylsulfinyl, $C_5-C_{20}$ arylsulfinyl, sulfonamido, amino, amido, imino, nitro, nitroso, hydroxyl, $C_1-C_{20}$ alkoxy, $C_5-C_{20}$ aryloxy, $C_2-C_{20}$ alkoxycarbonyl, $C_5-C_{20}$ aryloxycarbonyl, carboxyl, carboxylato, mercapto, formyl, $C_1-C_{20}$ thioester, cyano, cyanato, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{13}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen or phosphorus atom, or through an electron-rich metal or metalloid such as Ge, Sn, As, Sb, Se, Te, etc. With such functional groups, there will normally be an intervening linkage Z, such that $R^{13}$ then has the structure —$(Z)_n$—Fn wherein n is 1, Fn is the functional group, and Z is a hydrocarbylene linking group such as an alkylene, substituted alkylene, heteroalkylene, substituted heteroalkene, arylene, substituted arylene, heteroarylene, or substituted heteroarylene linkage.

J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —$(Z)_n$—Fn groups, wherein n is zero or 1, and Fn and Z are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefin reactants encompassed by structure (XIV) may be represented by the structure (XV)

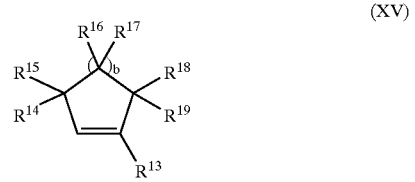

(XV)

wherein b is an integer generally although not necessarily in the range of 1 to 10, typically 1 to 5, $R^{13}$ is as defined above, and $R^{14}$, $R^{15}$, $R^{16}$, $R^{17}$, $R^{18}$, and $R^{19}$ are independently selected from the group consisting of hydrogen, hydrocarbyl, substituted hydrocarbyl, heteroatom-containing hydrocarbyl, substituted heteroatom-containing hydrocarbyl and —$(Z)_n$—Fn where n, Z and Fn are as defined previously, and wherein if any of the $R^{14}$ through $R^{19}$ moieties is substituted hydrocarbyl or substituted heteroatom-containing hydrocarbyl, the substituents may include one or more —$(Z)_n$—Fn groups. Accordingly, $R^{14}$, $R^{15}$, $R^{16}$, $R^{17}$, $R^{18}$, and $R^{19}$ may be, for example, hydrogen, hydroxyl, $C_1-C_{20}$ alkyl, $C_5-C_{20}$ aryl, $C_1-C_{20}$ alkoxy, $C_5-C_{20}$ aryloxy, $C_2-C_{20}$ alkoxycarbonyl, $C_5-C_{20}$ aryloxycarbonyl, amino, amido, nitro, etc. Furthermore, any of the $R^{14}$ through $R^{19}$ moieties can be linked to any other of the $R^{14}$ through $R^{19}$ moieties to provide a bicyclic or polycyclic olefin, and the linkage may include heteroatoms or functional groups, e.g., the linkage may include an ether, ester, thioether, amino, alkylamino, imino, or anhydride moiety.

Examples of monounsaturated, monocyclic olefins encompassed by structure (XV) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 1-methylcyclopentene, 4-methoxycyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by structure (XIV) may be generally represented by the structure (XVI)

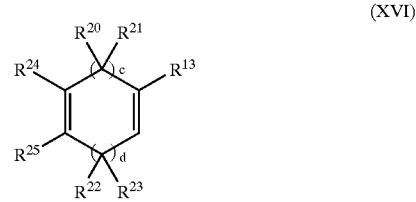

(XVI)

wherein c and d are independently integers in the range of 1 to about 8, typically 2 to 4, preferably 2 (such that the reactant is a cyclooctadiene), $R^{13}$ is as defined above, and $R^{20}$, $R^{21}$, $R^{22}$, $R^{23}$, $R^{24}$, and $R^{25}$ are defined as for $R^{14}$ through $R^{19}$. In this case, it is preferred that $R^{24}$ and $R^{25}$ be nonhydrogen substituents, in which case the second olefinic moiety is tetrasubstituted, so that the ROCM reaction proceeds selectively at only one of the two olefin functionalities. Examples of monocyclic diene reactants include, without limitation, 1,3-cyclopentadiene, 1,3-cyclohexadiene, 1,3-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene structure (XVI), and will generally contain at least one methylene linkage between any two olefinic segments.

Bicyclic and polycyclic olefinic reactants encompassed by structure (XIV) may be generally represented by the structure (XVII)

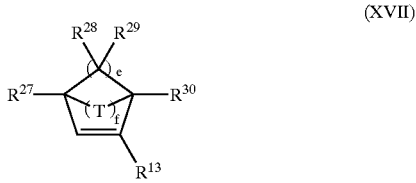

(XVII)

wherein e is an integer in the range of 1 to 8, typically 2 to 4, f is generally 1 or 2, T is lower alkylene or lower alkenylene, generally substituted or unsubstituted methyl or ethyl, $R^{13}$ is as defined above, and $R^{27}$, $R^{28}$, $R^{29}$, and $R^{30}$ are as defined for $R^{14}$ through $R^{19}$. Preferred olefinic reactants within this group are in the norbornene family, having the structure (XVIII)

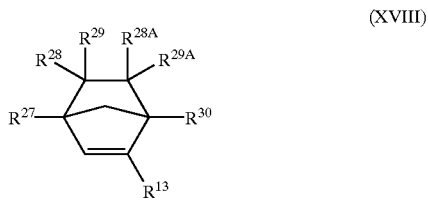

(XVIII)

wherein $R^{13}$, and $R^{27}$ through $R^{30}$ are as defined previously, and $R^{28A}$ and $R^{29A}$ are defined as for $R^{28}$ and $R^{29}$.

Examples of bicyclic and polycyclic olefinic reactants thus include, without limitation, dicyclopentadiene, tricyclopentadiene, dicyclohexadiene, norbornene, 5-methyl-2-norbornene, 5-ethyl-2-norbornene, 5-isobutyl-2-norbornene, 5,6-dimethyl-2-norbornene, 5-phenylnorbornene, 5-benzylnorbornene, 5-acetylnorbornene, 5-methoxycarbonylnorbornene, 5-methoxycarbonylnorbornene, 5-methyl-5-methoxycarbonylnorbornene, 5-cyanonorbornene, 5,5,6-trimethyl-2-norbornene, cyclo-hexenylnorbornene, endo, exo-5,6-dimethoxynorbornene, endo, endo-5,6-dimethoxynorbornene, endo,exo-5,6-dimethoxycarbonyl-norbornene, endo, endo-5,6-dimethoxycarbonylnorbornene, 2,3-dimethoxynorbornene, norbornadiene, tricycloundecene, tetracyclododecene, 8-methyltetracyclododecene, 8-ethyl-tetracyclododecene, 8-methoxycarbonyltetracyclododecene, 8-methyl-8-tetracyclo-dodecene, 8-cyanotetracyclododecene, pentacyclopentadecene, pentacyclohexadecene, 1,9-octadecadiene, and the like.

The second olefinic reactant is preferably one whose metathesis reactivity is not significantly higher or lower than that of the cyclic olefin, although, in some cases, for example when a monomeric product is preferred, a second olefin may be selected whose reactivity is somewhat higher than that of the cyloolefin. By reactivity is meant the relative rates at which the two reactants will undergo a metathesis reaction. More specifically, a cyclic olefin will undergo a ring opening reaction in the presence of the catalyst at a rate $k_{RO}$, and the second olefinic reactant will undergo a cross-metathesis reaction with the cyclic olefin at a rate $k_{CM}$. By appropriate selection of reactants, such that the approximate relationship of $k_{RO}$ to $k_{CM}$ is already known, i.e., predetermined, it is possible to control the selectivity of the reaction with regard to the resulting product. As illustrated in FIG. 1, when $k_{CM}$ is greater than or equal to $k_{RO}$, the ROCM product is predominantly a monomer, dimer, and/or oligomer, but not a polymer. When $k_{CM}$ is approximately equal to $k_{RO}$, the ROCM product is predominantly a dimer or oligomer, while when $k_{CM}$ is greater than $k_{RO}$, the ROCM product is predominantly a monomer. It will be appreciated that $k_{RO}$ will be higher for moderately and highly strained cycloolefins such as cyclooctadiene, but lower for low-strain olefins such as cyclopentene and cyclohexene.

Thus, the choice of the second olefinic reactant is virtually unlimited, although it should be a compound that (1) will undergo metathesis in the presence of the selected catalyst, (2) is not substituted with any functional groups that could adversely affect the desired outcome of the ROCM reaction, and (3) as discussed above, will undergo metathesis at a rate $k_{CM}$ such that the relative metathesis rates $k_{RO}$ and $k_{CM}$ optimize the production of the desired ROCM product, i.e., as a monomer, dimer, oligomer, or polymer, preferably as a dimer or oligomer. It will be appreciated that in the context of the present ROCM reaction, preferred second olefins are also incapable of undergoing a cross-metathesis reaction in the absence of any other olefinic reactants, i.e., the second olefin will not "self-react" via a metathesis pathway.

It is also important to note that both the cyclic olefin and the ROCM partner, i.e., the second olefinic reactant, can be substituted with functional groups that are not normally tolerated in olefin metathesis reaction. This significant advantage is provided by the transition metal alkylidene catalyst, described in the preceding section.

Exemplary second reactants are α,β-unsaturated carbonyl compound, e.g., an α,β-unsaturated aldehyde, an α,β-unsaturated ketone, or an enoic ester (i.e., an "α,β-unsaturated ester"). Such conjugated compounds generally have the structure (XIX)

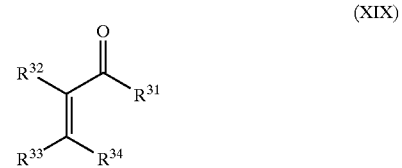

(XIX)

wherein $R^{31}$, $R^{32}$, $R^{33}$, and $R^{34}$ are independently selected from the group consisting of hydrogen, hydroxyl, hydrocarbyl (e.g., alkyl, cycloalkyl, aryl, alkaryl, aralkyl, etc.), substituted hydrocarbyl (e.g., substituted alkyl, cycloalkyl, aryl, alkaryl, aralkyl, etc.), heteroatom-containing hydrocarbyl (e.g., N, O, S, or P-containing cycloalkyl, aryl, alkaryl, aralkyl, etc.), substituted heteroatom-containing hydrocarbyl (e.g., substituted N, O, S, or P-containing cycloalkyl, aryl, alkaryl, aralkyl, etc.), and —$(Z)_n$—Fn where n, Z and Fn are defined previously, and further wherein, with substituted hydrocarbyl and substituted heteroatom-containing hydrocarbyl groups, the substituents may be, by way of example, halogen, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, amino, amido, nitro, and the like.

With preferred second reactants, $R^{31}$ is hydrogen, alkyl, hydroxyl, or alkoxy, $R^{32}$ and $R^{33}$ are hydrogen or alkyl, and $R^{34}$ is hydrogen.

As described in Examples 6 to 10, a series of experiments was carried out to evaluate ROCM reaction products obtained using the readily polymerizable substrate 1,5-cyclooctadiene (1,5-COD in Table 1). High yields of ROCM dimers analogous to that shown in FIG. 1 (when n is 1) were obtained under typical reaction conditions. A comparison of entries 1 and 2 reveals that the presence of a β-methyl group has little effect on product structure; the same dimer is formed in both cases. A similar product, containing three internal olefins, predominates for methyl vinyl ketone (entry 3). In contrast, crotonaldehyde and methacrolein result in monomeric species containing only one internal olefin (entries 4 and 5). If the stoichiometry of the acryloyl species is reduced relative to COD, a range of multiple oligomers that contain 4–10 internal alkenes predominates in the product mixtures.

TABLE 1

| entry | substrates | products | isolated yield |
|---|---|---|---|
| 1 | COD, 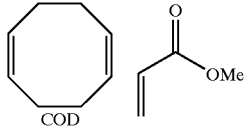 | 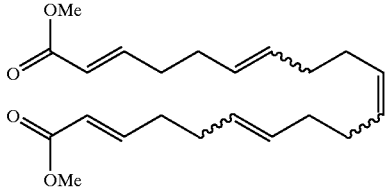 | 80% |
| 2 | COD, 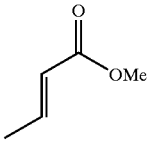 | 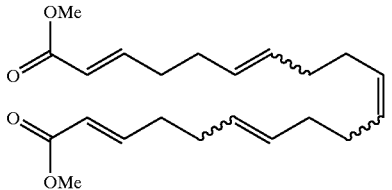 | 75% |
| 3 | COD, 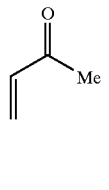 | 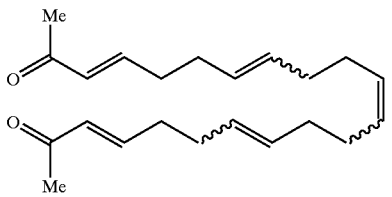 | 40% |
| 4 | COD, 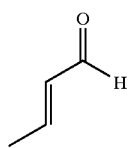 | 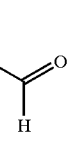 | 95% |
| 5 | COD, 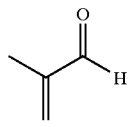 | 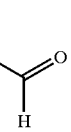 | 19% |

The methodology and catalyst complexes of the invention are useful not only in providing readily tunable ROCM reactions with a high strain cycloolefinic reactant, but are also effective with low strain cycloolefinic reactants, e.g., cyclopentene and cyclohexene. As described in Examples 11–15, ROCM reactions readily proceed between cyclohexene and several different reaction partners. The ROCM reaction partners, products obtained, and yields for the aforementioned examples are indicated below in Table 2. This achievement represents a significant advance in the art, insofar as a catalytic ring-opening metathesis reaction of low strain olefins such as cyclopentene and cyclohexene was not previously possible.

TABLE 2

| entry | substrates | products | isolated yield |
|---|---|---|---|
| 1 | 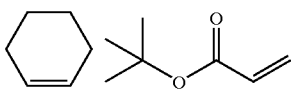 | 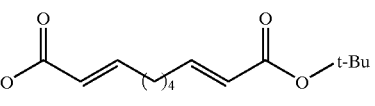 | 88% |
| 2 | 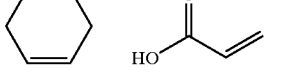 | 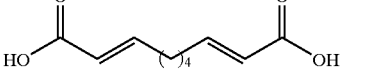 | 94% |

TABLE 2-continued

| entry | substrates | products | isolated yield |
|---|---|---|---|
| 3 |  | 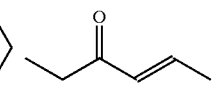 | 72% |
| 4 | 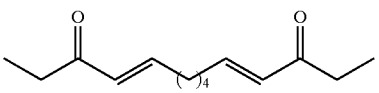 |  | 42% |

The present methodology and preferred catalysts are also useful for selectively synthesizing an asymmetrically terminated, or an "end-differentiated," olefin, as illustrated in FIG. 1 with respect to possible monomeric reaction products. In one embodiment, end differentiation is achieved by the choice of cyclic olefin is relevant, insofar as a 1,1,2-trisubstituted olefin will preferentially result in an asymmetrically terminated olefinic product. Alternatively, or in addition, end differentiation can be achieved in a two-step process wherein, initially, a first ROCM step is carried out as described in detail above, and a second step involves a simple cross metathesis reaction of an additional olefin with the ROCM product. In the latter step, the catalyst may or may not have the structure of formula (VII). Alternative catalysts for the second, cross-metathesis reaction include, for example, bisphosphine complexes, e.g., complexes having the structure of formula (V) wherein L and $L^1$ are phosphines of the formula $PR^5R^6R^7$, where $R^5$, $R^6$, and $R^7$ are each independently aryl or $C_1$–$C_{10}$ alkyl particularly primary alkyl, secondary alkyl or cycloalkyl (such as —P(cyclohexyl)$_3$, —P(cyclopentyl)$_3$, —P(isopropyl)$_3$), —P(phenyl)$_3$, —P(phenyl)$_2$($R^7$) and —P(phenyl)($R^7$)$_2$, in which $R^7$ is alkyl, typically lower alkyl. Such end-differentiated olefinic products, by virtue of their asymmetry, have enhanced utility with regard to subsequent synthetic processes.

As described in Examples 16 through 22, further experiments were carried out to evaluate various ROCM reactants with regard to selective preparation of an end-differentiated monomeric product. In order to suppress dimer formation, and in order to minimize formation of a symmetrical product, trisubstituted cycloolefins were selected as candidate substrates, and in fact did exhibit the desired selectivity. While not wishing to be bound by theory, we presume that trisubstituted cycloolefins are effective in this context because their ring opening is sufficiently slow to suppress dimer formation, and formation of a symmetrical product is disfavored due to the kinetically slow cross metathesis of acryloyl species onto geminally disubstituted olefins. As may be seen in Table 2, the acrylate is crossed onto the less substituted terminus, regardless of ring size, ring strain energy, or acryloyl cross partner.

However, the yields obtained with trisubstituted cycloolefin substrates appear to be dependent on the efficiency of ring opening. For example, the five-membered ring (Table 3, entry 1) exhibited a poor yield, presumably due to lower ring strain; higher strain cyclooctenes (entries 2–7) performed relatively well. Much higher yields for geminally disubstituted acroyl species (entry 4) were observed in contrast to unsubstituted COD cases. Dimethylcyclooctadiene (entries 6 and 7) could also be opened, leading to products with three differentiated alkenes: acroyl, geminally disubstituted, and trisubstituted. Importantly, all of the products in Table 3 can also be further functionalized by a cross metathesis on the geminally disubstituted terminus using previously disclosed methodology. Analogous substitution and stereoselectivity patterns were observed with substituted norbornenyl substrates, as illustrated schematically in FIG. 2.

TABLE 3

| entry | substrates | products | isolated yield |
|---|---|---|---|
| 1 | 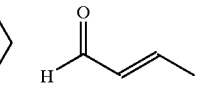 |  | 33% |
| 2 |  | 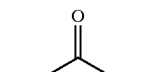 | 83% |
| 3 | 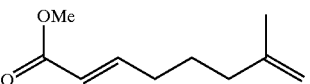 | 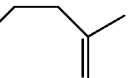 | 98% |

TABLE 3-continued

| entry | substrates | products | isolated yield |
|---|---|---|---|
| 4 | | | 67% |
| 5 | | | 57% |
| 6 | | | 66% (mixture) |
| 7 | | | 72% (mixture) |

As may be seen in Table 3, all of the reaction products obtained are capable of further functionalization by a cross metathesis on the geminally disubstituted terminus using an additional olefinic reactant.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental

NMR spectra were recorded on either an Inova 500 MHz or Oxford 300 MHz NMR spectrometer running Varian VNMR software. Chemical shifts are reported in parts per million (ppm) downfield from tetramethylsilane (TMS) with reference to internal solvent. Multiplicities are abbreviated as follows: singlet (s), doublet (d), triplet (t), quartet (q), quintet (quint), and multiplet (m). The reported $^1$H NMR and $^{13}$C NMR data refer to the major olefin isomer unless stated otherwise, and no peak assignments were made for the latter. High-resolution mass spectra (EI and CI) were provided by the University of California, Los Angeles Mass Spectrometry Facility. Product ratios were in part determined by gas chromatography/mass spectrometry using a Hewlett-Packard 5890 Gas Chromatograph interfaced with a HP 5970 series mass detector running HP ChemStation Software. Molecular mass calculations were performed with ChemDraw Ultra (Cambridge Scientific) or ChemIntosh Molecular Mass Calculator, version 1.3.

Analytical thin-layer chromatography (TLC) was performed using silica gel 60 F254 precoated plates (0.25 mm thickness) with a fluorescent indicator. Visualization was performed with either standard p-anisaldehyde or potassium permanganate stains. Flash column chromatography was performed using silica gel 60 (230–400 mesh) from EM Science. IMesH$_2$Cl was prepared according to a modified version of the procedure described in Scholl et al. (1999) Org. Lett. 1:953–956 and Jafarpour et al. (2000) Organometallics 19:2055–2057. All other chemicals were purchased from the Aldrich, Strem, TCI America, and ChemSampCo Chemical Companies, and used as obtained unless noted otherwise. Dimethylcyclooctadiene was obtained as a 4:1 mixture of 1,5- and 1,6-regioisomers and used without further separation. CH$_2$Cl$_2$ was purified and dried by passage through a solvent column and subsequently degassed (by N$_2$ purge) prior to use.

Preparation of IMesH$_2$Cl: IMesH$_2$Cl, used as a starting material in Examples 1 through 3, was synthesized according to the following scheme:

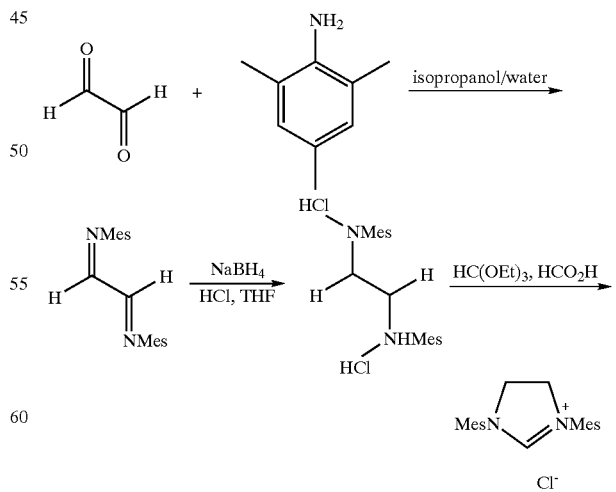

To a solution of glyoxal (9 mL, 79 mmol, 40% wt in H$_2$O) in isopropanol (100 mL) and H$_2$O (200 mL) was added mesitylamine (25 mL, 2.2 eq.) at 0° C. The reaction mixture was stirred while allowing to warm to room temperature. Immediately upon addition of amine, yellow precipitates were formed. After 24 hrs of stirring at ambient temperature, the precipitates were filtered and washed with $H_2O$ (1×100 mL) and hexanes (3×100 mL). The yellow precipitates obtained were dried in vacuo to yield the diimine (20.6 g, 89%).

To a solution of diimine (8.0 g, 27.3 mmol) in THF (100 mL) was added NaBH4 (4.24 g, 112.1 mmol) at 0° C. Concentrated HCl (4.5 mL, 2 eq.) was added dropwise over 30 minutes. After the HCl addition, the reaction mixture was stirred at 0° C. for 20 min. Then, 3 M HCl (250 mL) was added carefully to the flask at 0° C. and the mixture was stirred for an additional 1 hr, allowing the temperature to rise to ambient temperature. The resulting white precipitates were filtered and washed with water (200 mL) and 5% acetone-ether (150 mL). The product (9.4 g, 93%) was obtained as a white solid and dried in vacuo. To a suspension of the HCl salt (8.5 g, 23 mmol) in HC(OEt)3 (35 mL, 162 mmol) was added 2 drops of $HCO_2H$ (adding about 1 mol %). The reaction mixture was then heated at 120° C. for 5 hr under Ar. Then, the reaction mixture was cooled to an ambient temperature and hexane (200 mL) was added. The mixture was stirred for 1 hr and the white precipitates were filtered, washed with hexane (~200 mL) and dried in vacuo to yield the $IMesH_2HCl$ salt (7.6 g, 96%).

EXAMPLE 1

Synthesis of $RuCl_2(=CH—CH=C(CH_3)_2)(IMesH_2)$ $(PCy_3)$ (complex (2), Scheme 1):

SCHEME 1

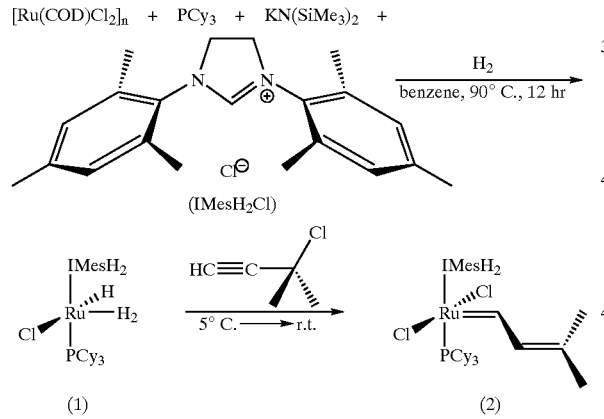

$[Ru(COD)Cl_2]_n$ (300 mg, 1 mmol), $IMesH_2Cl$ (1.47 g, 4 mmol), tricyclohexylphosphine (300 mg, 1 mmol), and $KN(SiMe_3)_2$ (540 mg, 2.5 mmol) were weighed directly into a 600 mL Schlenk tube. The flask was evacuated and filled with dry argon (2×). Degassed benzene (300 mL) was added and the flask was pressurized to 30 psi with $H_2$. The suspension was vigorously stirred for 12 hours at 90° C., yielding a bright yellow solution and white precipitate (1). After cooling the reaction to 5° C., propargyl chloride (0.3 mL, 4 mmol) was slowly added via syringe and the reaction mixture was allowed to warm to room temperature. The resulting brown benzene solution was washed with degassed 1M HCl (2×), degassed brine (2×), filtered through Celite and concentrated in vacuo to afford compound (2) as a brown solid in 90% yield (~95% purity). The brown solid displayed catalytic behavior identical with previously synthesized second-generation catalysts. Analytically pure (2) was obtained by column chromatography on silica gel (degassed 3:1 hexanes/$Et_2O$). $^1H$ NMR ($CD_2Cl_2$): δ 18.49 (d, J=11.1 Hz, 1H), 7.26 (d, J=10.9 Hz, 1H), 6.97 (s, 2H), 6.77 (s, 2H), 3.92 (m, 4H), 2.58 (s, 6H), 2.37 (s, 6H), 2.29 (s, 3H), 2.23 (s, 3H), 0.88–1.584 (m, 33H), 1.06 (s, 3H), 1.08 (s, 3H). $^{31}P$ NMR ($CD_2Cl_2$): δ 28.9. The reaction was repeated several times with one or more reaction conditions modified so as to optimize the yield of the product. It was found that the yield could be increased to greater than 95% by reducing the reaction temperature from 90° C. to 80° C.

Analogous ruthenium alkylidene complexes can be prepared using the aforementioned protocol and differently substituted phosphines, alkynes, etc., as indicated in the following two examples.

EXAMPLE 2

Synthesis of $RuCl_2(=CH—CH=C(CH_3)_2)(IMesH_2)$ $(PPh_3)$ (complex (4), Scheme 2):

SCHEME 2

$[Ru(COD)Cl_2]_n$ + $PPh_3$ + $KN(SiMe_3)_2$ +

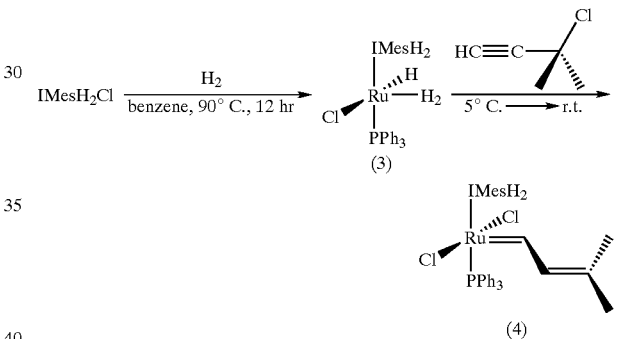

The procedure of Example 1 was employed using [Ru(COD)$Cl_2]_n$ (300 mg, 1 mmol), $IMesH_2Cl$ (0.74 g, 2 mmol), triphenylphosphine (280 mg, 1 mmol), and $KN(SiMe_3)_2$ (380 mg, 1.9 mmol), giving 550 mg (68%) of complex (4). $^{31}P$ NMR ($CD_2Cl_2$): δ 24.0. $^1H$ NMR ($CD_2Cl_2$): δ 18.49 (d, J=11.1 Hz, 1H).

EXAMPLE 3

Synthesis of $RuCl_2(=CH—CH—Ph)(IMesH_2)(PCy_3)$ (complex (5), Scheme 3):

SCHEME 3

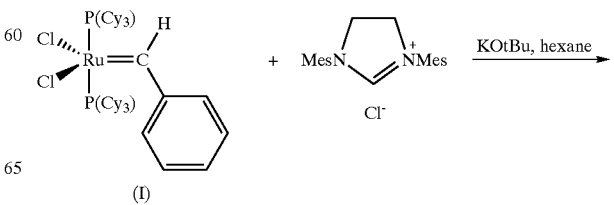

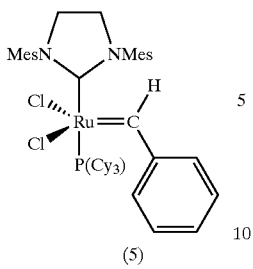

(5)

RuCl₂(=CHPh)(PCy₃)ₛ (phenylmethylene-bis(tricyclohexylphosphine) ruthenium dichloride, "catalyst (I)") (6.00 g, 7.29 mmol, 1.0 eq.), IMesH₂HCl salt prepared above (2 eq.), and potassium t-butoxide (2 eq.) were placed in a Schlenk flask. 60 mL of anhydrous degassed hexanes (Aldrich SureSeal bottle) were added. A vacuum was applied to further degas the reaction mixture, which was then heated to 60° C. for 24 hours. The suspension changed color from purple to orange-brown over the reaction time. After approximately 24 hr, the mixture was cooled to room temperature, and an excess of 1:1 isopropanol:water (180 mL) was added. The mixture was stirred rapidly in air for 30 min., then filtered using a medium porosity frit, and washed with isopropanol-water (3×100 mL) and hexanes (3×100 ML). The solids were dried in in vacuo, and the yield was approximately 75%. ¹H NMR (CD₂Cl₂, 400 MHz) δ 19.16 (s, 1H), 7.37–7.05 (m, 9H), 3.88 (s, 4H), 2.56–0.15 (m, 51H); ³¹P NMR (CD₂Cl₂, 161.9 MHz) δ 31.41; HRMS (FAB) C₄₅H₆₅Cl₂N₂PRu [M⁺] 848.3306, found 848.3286.

EXAMPLE 4

Synthesis of complex (6):

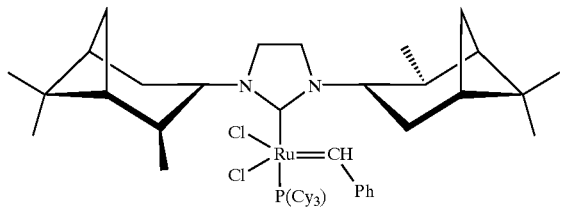

(6)

In a nitrogen-filled glovebox, a large Schlenk flask was charged with 0.475 g 1,3-(+)diisopinocamphenyl-4,5-dihydroimidazolium tetrafluoroborate salt [IPCimid(H)][BF₄] (1.120 mmol), 0.131 g potassium t-butoxide (1.120 mmol), and 30 mL anhydrous, degassed benzene. This mixture was stirred at room temperature for 6 hrs. Then, a solution of 0.400 g catalyst (I) (0.486 mmol) in 15 mL benzene was added, and the reaction was stirred for 30 min at room temperature, during which time the mixture changed from purple to brown. The reaction was concentrated to a third of its original volume under vacuum and transferred to a silica gel column (1.5×16"). The product was quickly eluted with 5:1 heptane:ether. The second, brown band was collected and stripped of solvent. The oily residue that remained was redissolved in a minimum amount of benzene and lyophilized to yield 0.080 g of the desired product as a brown powder (19%). ¹H NMR (299.817 MHz, 20° C., CD₂Cl₂): 20.583 and 20.577 [two s, two orientations of Ru=CHα], 8.54 [br s], 7.60 [t, J=7.3], 7.34 (t, J=7.8], 5.16 (qt, J=5.1], 3.46–3.96 [m], 2.86 (t, J=12.4], 2.34–2.50 [m], 1.44–2.20 [m], 1.43 (s), 1.41 (s), 0.82–1.31 [m], 1.26 [s], 1.12 [s], 1.01 [s], 0.57 [d, J=6.9], 0.25 [s]. ¹H NMR (299.817 MHz, −70° C., CD₂Cl₂): 20.32 [s, Ru=CHα], 9.07 [d, J=7.8], 7.87 [t, J=7.1], 7.59 [t, J=7.4], 7.35 [m], 4.92 [br], 3.30–3.90 [m], 2.69 [m], 2.44–0.78 [m], 1.33 [s], 1.16 [s], 1.02 [s], 0.90 [s], 0.88 [s], 0.86 [s], 0.80 [s], 0.78 [s], 0.43 [s], 0.11 [br d, J=5.7]. ³¹P{¹H} MR (121.39 MHz, 25° C., CD₂Cl₂): 21.72 [s]. ³¹P{¹H} NMR (121.39 MHz, −65° C., CD₂Cl₂): 21.95 [s], 21.16 [s].

EXAMPLE 5

Synthesis of complex (7):

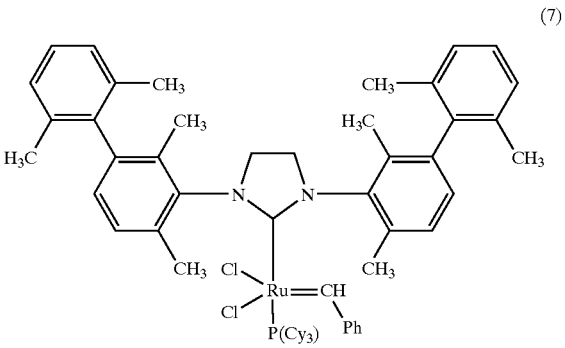

(7)

2-t-Butoxy-1,3-bis[2',6'-dimethyl-3'-(2",6"-dimethylphenyl)phenyl]-4,5-dihydroimidazol-2-ylidene was prepared by stirring a suspension of potassium tert-butoxide (9 mg, 0.080 mmol) and 1,3-bis[2',6'-dimethyl-3'-(2",6"-dimethylphenyl)-phenyl]4,5-dihydroimidazol-2-ylidene (50 mg, 0.079 mmol) in benzene (1 mL) for 1 h at room temperature. To this suspension was added catalyst (I) (65 mg, 0.079 mmol) in benzene (1 mL). The solution, which immediately became pinkish purple, was stirred at 50° C. for 16 h. After this time, the solution was cooled and the solvent was evaporated to near dryness. The residue was passed through a plug of TSI silica gel, using 1:1 ether/pentane as the eluant. After concentrating, the solids were washed with pentane (5×1 mL). The solid material was dissolved in benzene (1 mL) and was frozen (dry ice/acetone). The solvent was removed by sublimation to give phenylmethylene 1,3-bis[2',6'-dimethyl-2",6"-dimethylphenyl)phenyl]-4,5-dihydroimidazol-2-ylidene (50 mg, 62%) as a pink solid. ¹H NMR (500 mHz, toluene-d₈): δ=19.46 (s, 1H), 9.59 (br s, 1H), 7.35–6.18 (multiple peaks, 14H), 3.68–3.22 (multiple peaks, 4H), 2.98 (s, 3H), 2.61 (s, 3H), 2.46 (s, 3H), 2.35 (s, 3H), 2.19 (s, 3H), 1.98 (s, 3H), 1.92 (s, 3H), 2.09–1.10 (multiple peaks, 36H) ppm. ³¹P NMR (202 mHz, toluene-d₈): δ=34.54 ppm (s).

EXAMPLE 6

Representative Procedure for Ring-opening Cross-Metathesis Reactions (Table 1)

General procedure for ring-opening cross metathesis of cyclooctadiene with various acroyl species, as shown in Table 1, entry 1. A flame-dried round-bottomed flask equipped with reflux condenser was charged with 1,5-cyclooctadiene ("1,5-COD"; 43 mg, 0.4 mmol, 1.0 eq.), methyl acrylate (43 mg, 0.5 mmol, 1.3 eq.), and dry dichloromethane (1.0 mL). A solution of catalyst (5) (prepared as described in Example 3; 20 mg, 24 μmol, 0.05 eq.) in dichloromethane (1.0 mL) was subsequently added via cannula, producing a brick red solution, which was refluxed for 14 hours. The mixture was passed through a pipet plug of silica gel to remove the catalyst, and subsequently concentrated in vacuo to a yellow-brown oil. Purification of this residue by silica gel chromatography (7:3 hexanes:ethyl acetate) allows isolation of 56 mg of a clear yellow oil. (0.16 mmol, 78%, $R_f$=0.36). $^1$H NMR (300 MHz, CDCl$_3$, ppm): δ 6.96 (dt, J=6.6, 15.6 Hz, 2H), 5.82 (dm, J=2.7, 15.6 Hz, 2H), 5.40 (m, J=2.4, 3 Hz, 6H), 3.72 (s, 6H), 2.24 (t, J=7.8 Hz, 4H), 2.15 (t, J=4.8 Hz, 4H), 2.03 (m, J=1.5 Hz, 8 Hz). $^{13}$C NMR (125 MHz, CDCl$_3$, ppm): δ 167.1, 148.7, 131.0, 129.8, 128.8, 121.2, 51.4, 32.1, 31.6, 30.91, 30.86. HRMS (EI) calcd. for $C_{22}H_{33}O_4$ [M+H]$^+$361.2378, found 361.2382. The E:Z ratio of the internal olefins was determined by comparison of the multiplet at 5.40 ppm to the data reported for similar compounds (5.40 ppm for cis, 5.44 ppm for trans as reported in Hoye et al. (1986) *Tetrahedron* 42:2855–2862).

EXAMPLE 7

Ring-Opening Cross-Metathesis of 1,5-COD with Methyl Crotonate

The procedure of Example 6 was repeated with methyl crotonate instead of methyl acrylate (Table 1, entry 2), with relative stoichiometry as follows: 43 g (0.4 mmol, 1.0 eq.) 1,5-cyclooctadiene; 50 mg (0.5 mmol, 1.3 eq.) methyl crotonate; and 20 mg catalyst (5) (24 μmol, 0.05 eq.), in dichloromethane (2.0 mL). The crude product was purified by column chromatography (9:1 hexanes:ethyl acetate, $R_f$=0.43) resulting in 54 mg of a yellow oil (0.15 mmol, 75%). $^1$H and $^{13}$C NMR data are identical to those reported for Table 1, entry 1. HRMS (EI) calcd. for $C_{22}H_{33}O_4$ [M+H]$^+$361.2378, found 361.2379.

EXAMPLE 8

Ring-Opening Cross-Metathesis of 1,5-COD with Methyl Vinyl Ketone

The procedure of Example 6 was repeated with methyl vinyl ketone instead of methyl acrylate (Table 1, entry 3), with relative stoichiometry as follows: 43 g (0.4 mmol, 1.0 eq.) 1,5-cyclooctadiene; 36 mg (0.5 mmol, 1.3 eq.) methyl vinyl ketone; and 20 mg catalyst (5) (24 μmol, 0.05 eq.), in dichloromethane (2.0 mL). The crude product was purified by column chromatography (55:45 hexanes:ethyl acetate) resulting in 26 mg of a yellow oil corresponding to dimeric product (0.08 mmol, 39%, $R_f$=0.75) and 8 mg of a brownish yellow oil corresponding to terminal olefin product (0.04 mmol, 12%, $R_f$=0.55). $^1$H NMR (300 MHz, CDCl$_3$, ppm): δ 6.78 (dt, J=6.6, 15.9 Hz, 2H), 6.07 (dm, J=1.2, 15.9 Hz, 2H), 5.41 (m, J=2.4, 5.7 Hz, 6H), 2.27 (m, J=1.5, 6.6 Hz, 8H), 2.23 (s, 6H), 2.17 (m, J=1.8, 6.6 Hz, 8H). $^{13}$C NMR (125 MHz, CDCl$_3$, ppm): δ 198.7, 147.9, 131.6, 131.3, 128.9, 32.8, 32.7, 31.3, 27.1, 23.0. HRMS (EI) calcd. for $C_{22}H_{33}O_2$ [M+H]$^+$329.2480, found 329.2477.

EXAMPLE 9

Ring-Opening Cross-Metathesis of 1,5-COD with Crotonaldehyde

The procedure of Example 6 was repeated with crotonaldehyde instead of methyl acrylate (Table 1, entry 4), with relative stoichiometry as follows: 43 g (0.4 mmol, 1.0 eq.) 1,5-cyclooctadiene; 35 mg (0.5 mmol, 1.3 eq.) crotonaldehyde; and 20 mg catalyst (5) (24 μmol, 0.05 eq.), in dichloromethane (2.0 mL). The crude product was purified by column chromatography (7:3 hexanes:ethyl acetate, $R_f$=0.43) resulting in 46 mg of a yellow oil (0.24 mmol, 95%). $^1$H NMR (500 MHz, CDCl$_3$, ppm): δ 9.53 (d, J=14.5 Hz, 2H), 6.83 (dt, J=7.5, 15.6 Hz, 2H), 6.17 (dd, J=12.5, 25.5 Hz, 2H), 5.48 (m, J=2.5, 3.5 Hz, 2H), 2.43 (m, J=6.5 Hz, 4H), 2.25 (m, J=3.5, 14 Hz, 4H). $^{13}$C NMR (125 MHz, CDCl$_3$, ppm): δ 133.9, 157.6, 133.3, 129.7, 32.4, 30.6. HRMS (EI) calcd. for $C_{12}H_{15}O_2$ [M–H]$^+$191.1071, found 191.1073.

EXAMPLE 10

Ring-Opening Cross-Metathesis of 1,5-COD with Methacrolein

The procedure of Example 6 was repeated with methacrolein instead of methyl acrylate (Table 1, entry 5), with relative stoichiometry as follows: 43 g (0.4 mmol, 1.0 eq.) 1,5-cyclooctadiene; 2.1 mL methacrolein, and 20 mg catalyst (5) (24 μmol, 0.05 eq.), in dichloromethane (2.0 mL). The crude product was purified by column chromatography (9:1 hexanes:ethyl acetate, $R_f$=0.18) resulting in 17 mg of a yellow oil (0.07 mmol, 19%). $^1$H NMR (500 MHz, CDCl$_3$, ppm): δ 9.38 (s, 6H), 6.46 (td, J=1.5, 7.5 Hz, 2H), 5.48 (m, J=1.8, 2.1 Hz 2H), 2.40 (m, J=6.9 Hz, 4H), 2.21 (m, J=1.2, 5.1, 6.6 Hz, 2H), 1.73 (s, 6H) $^{13}$C NMR (125 MHz, CDCl$_3$, ppm): δ 195.2, 153.6, 139.6, 130.0, 31.1, 28.8. HRMS (EI) calcd. for $C_{14}H_{19}O_2$ [M–H]$^+$219.1384, found 219.1383.

EXAMPLE 11

Representative Procedure for Ring-Opening Cross-Metathesis of Cyclohexene with α,β-Unsaturated Carbonyl Compounds (Table 2)

The α,β-unsaturated carbonyl compound (1 eq.) and cyclohexene (3 eq.) were added via syringe to a flask charged with catalyst (5) (0.05 equiv in 0.05 to 0.4 M CH$_2$Cl$_2$). The flask was fitted with a condenser and refluxed under argon for 3 to 5 hours, and the progress of the reaction was monitored by TLC. After the solvent was evaporated, the product was purified directly on a silica gel column.

EXAMPLE 12

Ring-Opening Cross-Metathesis of Cyclohexene with Acrylic Acid, T-butyl Ester The general procedure of Example 11 was carried out using cyclohexene and acrylic acid, t-butyl ester, as reactants (Table 2, entry 1). The product was purified directly on a silica gel column, eluting with 1:15=ethyl acetate:hexane. 28.0 mg of the product was obtained ($R_f$=0.4 in 1:10= EA:Hx, clear oil). $^1$H NMR (300 MHz, CDCl$_3$, ppm): δ 6.80 (2H, dt, J=15.6 Hz, 6.9 Hz), 5.70 (2H, d, J=15.9 Hz), 2.14 (4H, m), 1.44 (22H, m) $^{13}$C NMR (75 MHz, CDCl$_3$, ppm): 166.2, 147.6, 123.4, 80.3, 32.1, 28.5, 27.9. HRMS (EI) calcd for $C_{18}H_{30}O_4$ 310.2144, found 310.2151.

EXAMPLE 13

Ring-Opening Cross-Metathesis of Cyclohexene with Acrylic Acid

The procedure of Example 12 was repeated except that acrylic acid was used instead of its t-butyl ester (Table 2, entry 2). The product was purified directly by filtering and washed with dichloromethane; 29.1 mg of the product was obtained (white solid). $^1$H NMR (300 MHz, THF-d8, ppm): δ 10.64 (2H, s), 6.80 (2H, dt, J=15.6, 6.3 Hz), 5.75 (2H, d, J=15.6 Hz), 2.20 (4H, m), 1.50 (4H, m). $^{13}$C NMR (75 MHz, THF-d8, ppm): δ 168.3, 149.9, 123.9, 33.8, 29.8. HRMS (EI) calcd for $C_{10}H_{14}O_4$ 198.0893, found 198.0896.

EXAMPLE 14

Ring-Opening Cross-Metathesis of Cyclohexene with Hex-4-en-3-one

The procedure of Example 12 was repeated except that hex-4-en-3-one was used instead of the t-butyl ester of acrylic acid (Table 2, entry 3). The product was purified directly on a silica gel column, eluting with 1:4=ethyl acetate:hexane. 15.4 mg of the product was obtained ($R_f$ 0.3 in 1:3=EA:Hx, clear oil). $^1$H NMR (300 MHz, CDCl$_3$, ppm): δ 6.80 (2H, dt, J=15.6 Hz, 6.9 Hz), 6.05 (2H, d, J=15.6 Hz), 2.52 (4H, q, J=7.5 Hz), 2.19 (4H, m), 1.47 (4H, m), 1.06 (6H, t, J=7.2 Hz). $^{13}$C NMR (75 MHz, CDCl$_3$, ppm): 201.1, 146.4, 130.5, 39.7, 32.5, 28.0, 8.5. HRMS (EI) calcd for $C_{14}H_{22}O_2$ 222.1620, found 222.1622.

EXAMPLE 15

Ring-opening Cross-metathesis of Cyclohexene with But-2-enal

The procedure of Example 12 was repeated except that but-2-enal was used instead of the t-butyl ester of acrylic acid (Table 2, entry 4). The product was purified directly on a silica gel column, eluting with 1:2=ethyl acetate: hexane; 7.4 mg of the product was obtained ($R_f$=0.3 in 1:2=EA:Hx, clear oil). $^1$H NMR (300 MHz, CDCl$_3$, ppm): δ 9.49 (2H, d, J=7.8 Hz), 6.80 (2H, dt, J=15.6 Hz, 6.9 Hz), 6.10 (2H, ddt, J=15.6, 7.8, 1.5 Hz), 1.47 (4H, m).

EXAMPLE 16

Representative Procedures for Ring-Opening Cross-Metathesis of Trisubstituted Cycloolefins with Acryloyl Species (Table 3)

A solution of catalyst (5) and dry dichloromethane was added via cannula to a flame-dried round-bottomed flask equipped with reflux condenser and kept under slight argon pressure. The cycloolefin and acryloyl cross partner were added to the flask via syringe. The brick red solution was refluxed for 14 hours. The mixture was then concentrated in vacuo to a yellowish brown oil. Products were purified by silica gel chromatography (19:1 or 8:2 hexanes:ethyl acetate), yielding oils in all cases.

EXAMPLE 17

Ring-Opening Cross-Metathesis of 1-methylcyclopentene with Methyl Acrylate

The procedure of Example 16 was carried out with 1-methylcyclopentene and methyl acrylate as reactants (Table 3, entry 1), with relative stoichiometry as follows: 134 µL 1-methylcyclopentene (1.2 mmol, 3.0 eq.), 36 µL methyl acrylate (0.4 mmol, 1.0 eq.), and 17 mg catalyst (5) (20 µmol, 0.05 eq.), in dichloromethane (1 mL). The crude product was purified by column chromatography (19:1 hexanes:ethyl acetate), resulting in 22 mg of a light yellow oil. $^1$H NMR (300 MHz, CDCl$_3$, ppm): δ 6.98 (1H, dt, J=15.6, 6.9 Hz), 5.83 (1H, dt, J=15.6, 1.8 Hz), 4.73 (1H, s), 4.68 (1H, s), 3.73 (3H, s), 2.21 (2H, dtd, J=7.2, 7.2, 1.5 Hz), 2.04 (2H, t, J=7.5 Hz), 1.71 (3H, s), 1.6 (2H, m). $^{13}$C NMR (300 MHz, CDCl$_3$, ppm): δ 167.0, 149.3, 145.0, 121.0, 110.3, 51.5, 37.1, 31.7, 25.9, 22.4. HRMS (DCI): calcd. for $C_{10}H_{17}O_2$ [M+H]$^+$169.1229, found: 169.1231.

EXAMPLE 18

Ring-Opening Cross-Metathesis of 1-methylcyclooctene with Methyl Acrylate

The procedure of Example 16 was repeated with 1-methylcyclooctene instead of 1-methylcyclopentene (Table 3, entry 2), with relative stoichiometry as follows: 30 µL 1-methylcyclooctene (0.2 mmol, 1.0 eq.), 36 µL methyl acrylate (0.4 mmol, 1.0 eq.), and 8 mg catalyst (5) (9.4 µmol, 0.05 eq.), in dichloromethane (5 mL). The crude product was purified by column chromatography (19:1 hexanes:ethyl acetate), resulting in 35 mg of a light yellow oil. $^1$H NMR (300 MHz, CDCl$_3$, ppm): δ 6.96 (1H, dt, J=15.6, 6.9 Hz), 5.81 (1H, dt, J=15.9, 1.5 Hz), 4.67 (1H, s), 4.64 (1H, s), 3.71 (3H, s), 2.19 (2H, dtd, J=7.2, 7.2, 1.5 Hz), 1.98 (2H, t, J=7.5 Hz), 1.69 (3H, s), 1.4 (8H, m). $^{13}$C NMR (300 MHZ, CDCl$_3$, ppm): δ 167.0, 150.0, 145.9, 120.7, 109.6, 51.4, 37.8, 32.2, 29.1, 28.0, 27.5, 22.4. HRMS (DCI) calcd. for $C_{13}H_{23}O_2$ [M+H]$^+$211.1698, found 211.1693.

EXAMPLE 19

Ring-Opening Cross-Metathesis of 1-methylcyclooctene with T-Butyl Acrylate

The procedure of Example 18 was repeated with t-butyl acrylate instead of methyl acrylate (Table 3, entry 3), with relative stoichiometry as follows: 30 µL 1-methylcyclooctene (0.2 mmol, 1.0 eq.), 60 µL methyl acrylate (0.4 mmol, 2.0 eq.), and 8 mg catalyst (5) (9.4 µmol, 0.05 eq.), in dichloromethane (5 mL). The crude product was purified by column chromatography (19:1 hexanes:ethyl acetate), resulting in 63 mg of a light yellow oil. $^1$H NMR (300 M Hz, CDCl$_3$, ppm): δ 6.84 (1H, dt, J=15.6, 7.2 Hz), 5.71 (1H, dt, J=15.6, 1.7 Hz), 4.67 (1H, s), 4.64 (1H, s), 2.15 (2H, dt, J=6.8, 6.8 Hz), 1.98 (2H, t, J=7.7 Hz), 1.69 (3H, s), 1.47 (9H, s), 1.4 (8H, m). $^{13}$C NMR (300 M Hz, CDCl$_3$, ppm): δ 166.0, 148.0, 146.0, 122.8, 109.6, 79.9, 37.8, 32.1, 29.09, 29.08, 28.2, 28.1, 27.5, 22.4. HRMS (EI): calcd. for $C_{16}H_{28}O_2$ [M]$^+$252.2089, found: 252.2094. In addition to the product described above, this oil contained approximately 20% t-butyl acrylate dimer, which is characterized in Choi et al. (2001) *J. Am. Chem. Soc.* 123, 10417–18.

EXAMPLE 20

Ring-Opening Cross-Metathesis of 1-Methylcyclooctene with Methyl Methacrylate

The procedure of Example 18 was repeated with methyl methacrylate instead of methyl acrylate (Table 3, entry 4), with relative stoichiometry as follows: 30 µL 1-methylcyclooctene (0.2 mmol, 1.0 eq.), 1 mL methyl methacrylate (9.3 mmol, 47 eq.), and 8 mg catalyst (5) (9.4 µmol, 0.05 eq.). The crude product was purified by column chromatography (19:1 hexanes:ethyl acetate), resulting in 30 mg of an orange oil. $^1$H NMR (300 M Hz, CDCl$_3$, ppm): δ 6.76 (1H, td, J=7.6, 1.3 Hz), 4.68 (1H, s), 4.65 (1H, s), 3.73 (3H, s), 2.17 (2H, dt, J=7.0, 7.0 Hz), 2.00 (2H, t, J=7.4 Hz), 1.83 (3H, s), 1.71 (3H, s), 1.4 (8H, m). $^{13}$C NMR (300 M Hz, CDCl$_3$, ppm): δ 168.6, 146.0, 142.62, 127.26, 109.54, 51.69, 37.79, 29.27, 29.13, 28.69, 28.57, 27.53, 22.44, 12.45. HRMS (EI) calcd. for $C_{14}H_{24}O_2$ [+H]$^+$, actual data will be supplied as it becomes available.

EXAMPLE 21

Ring-Opening Cross-Metathesis of 1-Methylcyclooctene with Methyl Vinyl Ketone

The procedure of Example 18 was repeated with methyl vinyl ketone instead of methyl acrylate (Table 3, entry 5), with relative stoichiometry as follows: 30 μL 1-methylcyclooctene (0.2 mmol, 1.0 eq.), 18 μL methyl vinyl ketone (0.2 mmol, 1.0 eq.), and 8 mg catalyst (5) (9.4 μmol, 0.05 eq.) in dichloromethane (10 mL). The crude product was purified by column chromatography (8:2 hexanes:ethyl acetate), resulting in 22 mg of a yellow-orange oil. $^1$HNMR (300 M Hz, CDCl$_3$, ppm): δ 6.80 (1H, dt, J=15.6, 6.9 Hz), 6.06 (1H, d, J=16.2 Hz), 4.68 (1H, s), 4.65 (1H, s), 2.24 (3H, s), 2.2 (2H, m), 2.00 (2H, t, J=7.7 Hz), 1.71 (3H, s), 1.4 (8H, m). $^{13}$CNMR (300 M Hz, CDCl$_3$, ppm): δ 198.5, 148.4, 145.9, 131.2, 109.6, 37.8, 32.5, 29.11, 29.05, 28.1, 27.5, 26.9, 22.4. HRMS (EI): calcd. for C$_{13}$H$_{22}$O [M]$^+$:194.1671, found: 194.1670.

EXAMPLE 22

Ring-Opening Cross-Metathesis of 1,5-Dimethyl-1,5-cyclooctadiene with Methyl Acrylate The procedure of Example 18 was repeated with 1,5-dimethyl-1,5-cyclooctadiene instead of 1-methylcyclooctene (Table 3, entry 6), with relative stoichiometry as follows: 96 μL 1,5-dimethyl-1,5-cyclooctadiene (0.6 mmol, 3.0 eq.), 18 μL methyl acrylate (0.2 mmol, 1.0 eq.), and 8 mg catalyst (5) (9.4 μmol, 0.05 eq.) in dichloromethane (20 mL). The crude product was purified by column chromatography (19:1 hexanes:ethyl acetate), resulting in 32 mg of an orange oil. $^1$HNMR (300 MHz, CDCl$_3$, ppm): δ 6.96 (1H, dt, J=15.6, 6.6 Hz), 5.83 (1H, dt, J=15.6, 1.5 Hz), 5.17 (1H, t, J=6.9 Hz), 4.71 (1H, s), 4.67 (1H, s), 3.72 (3H, s), 2.2 (8H, m), 1.72 (3H, s), 1.69 (3H, s). $^{13}$CNMR (300 MHz, CDCl$_3$, ppm): δ 166.9, 149.0, 145.5, 133.5, 125.8, 120.9, 109.9, 51.4, 37.9, 30.7, 30.4, 26.1, 23.3, 22.6. HRMS (CI) calcd. for C$_{14}$H$_{23}$O$_2$ [M+H]$^+$ 223.1698, found 223.1691.

EXAMPLE 23

Ring-Opening Cross-Metathesis of 1,5-Dimethyl-1,5-cyclooctadiene with T-butyl Acrylate The procedure of Example 22 was repeated with t-butyl acrylate instead of methyl acrylate (Table 2, entry 8), with relative stoichiometry as follows: 96 μL 1,5-dimethyl-1,5-cyclooctadiene (0.6 mmol, 3.0 eq.), 30 μL methyl acrylate (0.2 mmol, 1.0 eq.), and 8 mg catalyst (5) (9.4 μmol, 0.05 eq.) in dichloromethane (20 mL). The crude product was purified by column chromatography (19:1 hexanes:ethyl acetate), resulting in 44 mg of a light orange oil. $^1$HNMR (300 M Hz, CDCl$_3$, ppm): δ 6.85 (1H, dt, J=15.9, 6.6 Hz), 5.75 (1H, dt, J=15.3, 1.5 Hz), 5.17 (1H, t, J=6.8 Hz), 4.71 (1H, s), 4.67 (1H, s), 2.1 (8H, m), 1.72 (3H, s), 1.69 (3H, s), 1.48 (9H, s). $^{13}$CNMR (300 M Hz, CDCl$_3$, ppm): δ 165.8, 147.3, 145.5, 133.7, 125.7, 123.0, 109.9, 80.0, 38.0, 30.6, 30.5, 28.2, 26.1, 23.3, 22.6. HRMS (EI) calcd. for C$_{17}$H$_{28}$O$_2$ [M]$^+$264.2089, found: 264.2084.

EXAMPLE 24

Ring-Opening Cross-Metathesis of Substituted Norbornenes with Acryloyl ROCM Partners Methyl acrylate (1.1 eq.) and the substituted norbornene compound (1 eq.) were added via syringe to a flask charged with catalyst (5) (0.05 eq. in CH$_2$Cl$_2$). The flask was fitted with a condenser and refluxed under argon for 3 to 5 hours, and the progress of the reaction was monitored by TLC. After the solvent was evaporated, the product was purified directly on a silica gel column. The substituted norbornene compounds evaluated were: (1) 1-methyl-bicyclo[2.2.1]hept-5-ene-2,3-dicarboxylic acid dimethyl ester, having the structure

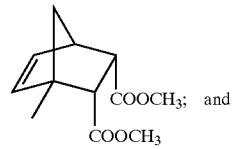

(2) a 92%/8% admixture of 8-methyl-4-oxa-tricyclo[5.2.1.0$^{2,6}$]dec-8-ene-3,5-dione and 1-methyl-4-oxa-tricyclo[5.2.1.0$^{2,6}$]dec-8-ene-3,5-dione, i.e.,

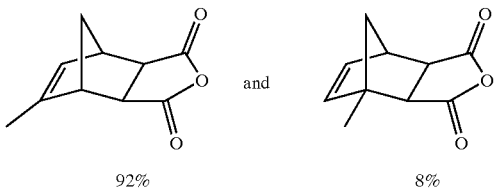

(all exo). As may be seen in FIG. 2, the ROCM reaction with the diester and methyl acrylate resulted in a 60% yield of the cis-disubstituted product. The ROCM reaction with the anhydride admixture and methyl acrylate provided an asymmetrically substituted product resulting from ROCM of the disubstituted olefin, with full recovery of the trisubstituted substrate.

Figure 2:
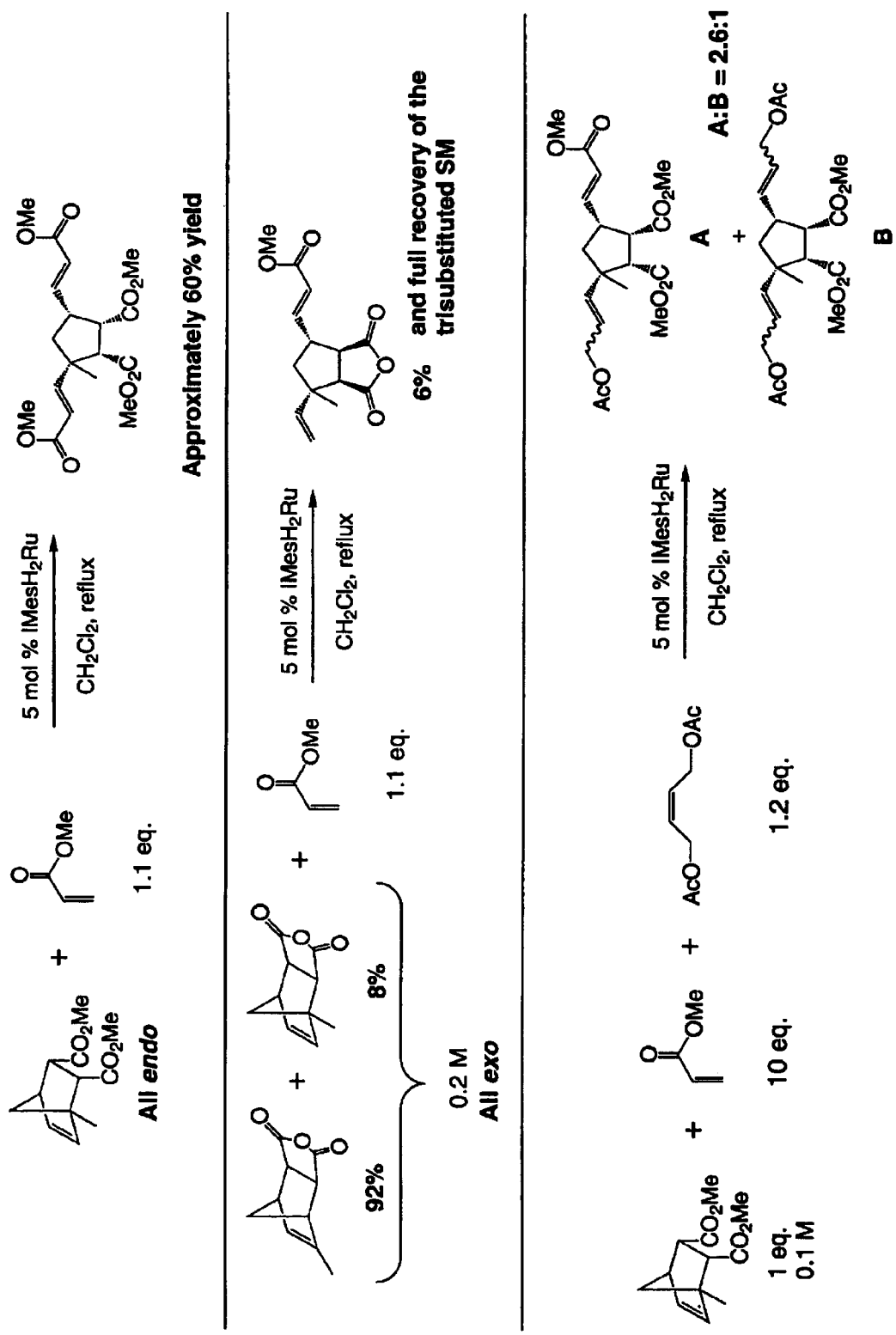
FIG. 2 schematically illustrates the results of ROCM reactions carried out according to the present invention, using either a norbornenyl diester or a norbornenyl anhydride as the cycloolefin substrate and methyl acrylate as a reaction partner.

Methyl acrylate (10 eq.), but-2-ene-1,4-diacetate (1.2 eq.) and 1-methyl-bicyclo[2.2.1]hept-5-ene-2,3-dicarboxylic acid dimethyl ester (1 eq.) were added via syringe to a flask charged with catalyst (5) (0.05 eq. in CH$_2$Cl$_2$). The flask was fitted with a condenser and refluxed under argon for 3 to 5 hours, and the progress of the reaction was monitored by TLC. After the solvent was evaporated, the product was purified directly on a silica gel column. As indicated in FIG. 2, the ratio of the end-differentiated olefinic product to the symmetrically terminated product was 2.6:1.

We claim:

1. A method for carrying out a ring-opening cross-metathesis (ROCM) reaction between a cyclic olefin and a second olefinic reactant to provide an ROCM product, comprising contacting the cyclic olefin with the second olefinic reactant in the presence of a catalyst composed of a Group 8 transition metal alkylidene complex under conditions and for a time period effective to allow the ROCM reaction to occur, wherein the catalyst has the structure of formula (VII)

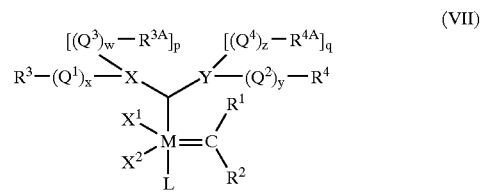

in which:
M is a Group 8 transition metal;
X$^1$ and X$^2$ may be the same or different, and are anionic ligands or polymers;
R$^1$ is selected from the group consisting of hydrogen, hydrocarbyl, substituted hydrocarbyl, heteroatom-containing hydrocarbyl, substituted heteroatom-containing hydrocarbyl, and carboxyl;

$R^2$ is selected from the group consisting of hydrogen, hydrocarbyl, substituted hydrocarbyl, heteroatom-containing hydrocarbyl, and substituted heteroatom-containing hydrocarbyl;

L is a neutral electron donor ligand;

X and Y are heteroatoms selected from N, O, S, and P;

p is zero when X is O or S, and is 1 when X is N or P;

q is zero when Y is O or S, and is 1 when Y is N or P;

$Q^1$, $Q^2$, $Q^3$, and $Q^4$ are selected from hydrocarbylene, substituted hydrocarbylene, heteroatom-containing hydrocarbylene, substituted heteroatom-containing hydrocarbylene, and —(CO)—;

w, x, y and z are independently zero or 1; and $R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein any two or more of $X^1$, $X^2$, L, $R^1$, $R^2$, $R^3$, $R^{3A}$, $R^4$, and $R^{4A}$ can be taken together to form a chelating multidentate ligand.

2. The method of claim 1, wherein the cyclic olefin undergoes a ring opening reaction in the presence of the catalyst at a rate $k_{RO}$, the second olefinic reactant undergoes a cross-metathesis reaction with the cyclic olefin at a rate $k_{CM}$, and the approximate relationship of $k_{RO}$ to $k_{CM}$ is predetermined.

3. The method of claim 2, wherein $k_{CM}$ is greater than or equal to $k_{RO}$, such that the ROCM product is predominantly a monomer, dimer, and/or oligomer, but not a polymer.

4. The method of claim 3, wherein $k_{CM}$ is approximately equal to $k_{RO}$, such that the ROCM product is predominantly a dimer or oligomer.

5. The method of claim 3, wherein $k_{CM}$ is greater than $k_{RO}$, such that the ROCM product is predominantly a monomer.

6. The method of claim 5, wherein the cyclic olefin is a 1,1,2-trisubstituted olefin, such that the monomer product is predominantly asymmetrically terminated.

7. The method of claim 3, wherein the cyclic olefin contains 4 to about 12 carbon atoms and is substituted with zero to about 4 nonhydrogen substituents.

8. The method of claim 7, wherein the cyclic olefin is monocyclic.

9. The method of claim 7, wherein the cyclic olefin is bicyclic.

10. The method of claim 7, wherein the cyclic olefin contains 1 to 3 double bonds.

11. The method of claim 10, wherein the cyclic olefin contains 1 double bond.

12. The method of claim 10, wherein the cyclic olefin contains 2 double bonds.

13. The method of claim 7, wherein at least one of the nonhydrogen substituents comprises a functional group Fn selected from phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, and germyl.

14. The method of claim 1, wherein the second olefinic reactant is incapable of undergoing a cross-metathesis reaction in the absence of any other olefinic reactants.

15. The method of claim 14, wherein the second olefinic reactant is an α,β-unsaturated carbonyl compound.

16. The method of claim 13, wherein the second olefinic reactant is also substituted with at least one functional group Fn.

17. The method of claim 1, wherein:

$X^1$ and $X^2$ are anionic ligands, and are optionally linked to form a cyclic group;

L is a neutral electron donor ligand that is optionally linked to $R^2$, $X^1$, and/or $X^2$ through a spacer moiety; and $R^{3A}$ and $R^{4A}$ are optionally linked to form a cyclic group.

18. The method of claim 1, wherein w, x, y and z are zero, X and Y are N, and $R^{3A}$ and $R^{4A}$ are linked to form —Q—, such that the catalyst has the structure of formula (IX)

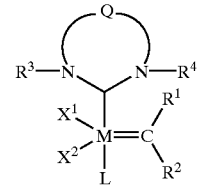

(IX)

wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group.

19. The method of claim 18, wherein Q has the structure —$CR^8R^{8A}$—$CR^9R^{9A}$— or —$CR^8$=$CR^9$—, wherein $R^8$, $R^{8A}$, $R^9$, and $R^{9A}$ are independently selected from the group consisting of hydrogen, hydrocarbyl, substituted hydrocarbyl, heteroatom-containing hydrocarbyl, substituted heteroatom-containing hydrocarbyl, and functional groups, wherein any two of $R^8$, $R^{8A}$, $R^9$, and $R^{9A}$ are optionally linked to form a substituted or unsubstituted, saturated or unsaturated ring.

20. The method of claim 19, wherein Q has the structure —$CR^8R^{8A}$—$CR^9R^{9A}$—, such that the catalyst has the structure of formula (X)

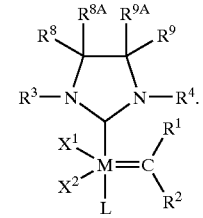

(X)

21. The method of claim 20, wherein:

M is Ru;

$X^1$ and $X^2$ may be the same or different, and are selected from the group consisting of hydrogen, halide, $C_1$–$C_{20}$ alkyl, $C_5$–$C_{20}$ aryl, $C_1$–$C_{20}$ alkoxy, $C_5$–$C_{20}$ aryloxy, $C_3$–$C_{20}$ alkyldiketonate, $C_5$–$C_{20}$ aryldiketonate, $C_2$–$C_{20}$ alkoxycarbonyl, $C_5$–$C_{20}$ aryloxycarbonyl, $C_2$–$C_{20}$ acyl, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl, any of which, with the exception of halide, are optionally further substituted with one or more groups selected from halide, $C_1$–$C_6$ alkyl, $C_1$–$C_6$ alkoxy, and phenyl;

R¹ is hydrogen and R² is selected from the group consisting of $C_1$–$C_{20}$ alkyl, $C_2$–$C_{20}$ alkenyl, and aryl;

L is a neutral electron donor ligand selected from the group consisting of phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether;

R³ and R⁴ are aromatic, substituted aromatic, heteroaromatic, substituted heteroaromatic, alicyclic, substituted alicyclic, heteroatom-containing alicyclic, or substituted heteroatom-containing alicyclic, composed of from one to about five rings; and R⁸ and R⁹ are hydrogen, and $R^{8A}$ and $R^{9A}$ are selected from hydrogen, lower alkyl and phenyl, or are linked to form a cyclic group.

22. The method of claim 21, wherein:

R¹ is hydrogen, and R² is phenyl, vinyl, methyl, isopropyl, or t-butyl, optionally substituted with one or more moieties selected from the group consisting of $C_1$–$C_6$ alkyl, $C_1$–$C_6$ alkoxy, phenyl, and a functional group Fn, wherein Fn is phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, or germyl; and L is a phosphine of the formula $PR^5R^6R^7$, where R⁵, R⁶, and R⁷ are each independently aryl or $C^1$–$C^{10}$ alkyl.

23. The method of claim 22, wherein:

X¹ and X² are independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate;

L is selected from the group consisting of —P(cyclohexyl)₃, —P(cyclopentyl)₃, —P(isopropyl)₃, —P(phenyl)₃, P(phenyl)₃, —P(phenyl)₂(R⁷) and —P(phenyl)(R⁷)₂, in which R⁷ is lower alkyl; and R³ and R⁴ are the same and are either aromatic or $C_7$–$C_{12}$ alicyclic, if aromatic, each having the structure of formula (XI)

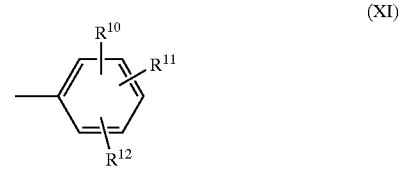

(XI)

in which $R^{10}$, $R^{11}$, and $R^{12}$ are each independently hydrogen, $C_1$–$C_{10}$ alkyl, $C_1$–$C_{10}$ alkoxy, aryl, substituted aryl, halogen, or a functional group.

24. The method of claim 23, wherein:

X¹ and X² are halide;

R² is hydrogen or 2,2-dimethylvinyl;

R³ and R⁴ are mesityl, diisopinocamphenyl, or 2,4,2',6'-tetramethylbiphenylyl;

L is selected from the group consisting of —P(cyclohexyl)₃ and —P(cyclopentyl)₃; and $R^{8A}$ and $R^{9A}$ are hydrogen.

25. The method of claim 1, further including reacting the ROCM product with an additional olefinic reactant capable of undergoing cross-metathesis therewith, in the presence of a transition metal catalyst.

26. The method of claim 15, wherein the cyclic olefin is cyclohexene.

* * * * *